US009255924B2

(12) United States Patent
Schorey et al.

(10) Patent No.: US 9,255,924 B2
(45) Date of Patent: Feb. 9, 2016

(54) EXOSOMES AND DIAGNOSTIC BIOMARKERS

(71) Applicants: University of Notre Dame du Lac, Notre Dame, IN (US); Colorado State University Research Foundation, Fort Collins, CO (US)

(72) Inventors: Jeffrey S. Schorey, Granger, IN (US); Karen M. Dobos, Fort Collins, CO (US)

(73) Assignees: University of Notre Dame du Lac, Notre Dame, IN (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/052,378

(22) Filed: Oct. 11, 2013

(65) Prior Publication Data

US 2014/0113305 A1   Apr. 24, 2014

Related U.S. Application Data

(60) Provisional application No. 61/795,220, filed on Oct. 12, 2012.

(51) Int. Cl.
| | |
|---|---|
| *A61K 39/04* | (2006.01) |
| *C12N 1/20* | (2006.01) |
| *G01N 33/569* | (2006.01) |
| *G01N 33/68* | (2006.01) |
| *C07K 14/35* | (2006.01) |

(52) U.S. Cl.
CPC ............ *G01N 33/5695* (2013.01); *A61K 39/04* (2013.01); *G01N 33/6848* (2013.01); *C07K 14/35* (2013.01); *G01N 2333/35* (2013.01)

(58) Field of Classification Search
None
See application file for complete search history.

(56) References Cited

U.S. PATENT DOCUMENTS

| | | |
|---|---|---|
| 2009/0148460 A1 | 6/2009 | Declayre |
| 2010/0143916 A1 | 6/2010 | Liew |
| 2012/0238467 A1 | 9/2012 | Taylor |
| 2012/0309041 A1 | 12/2012 | Timmers |
| 2013/0005599 A1 | 1/2013 | Klass |
| 2013/0157888 A1 | 6/2013 | Nagele |
| 2013/0225662 A1 | 8/2013 | Kennedy |
| 2013/0287772 A1 | 10/2013 | Halbert |
| 2013/0323756 A1 | 12/2013 | Tullis |

OTHER PUBLICATIONS

Rosenkrands 2000 Electrophoresis, 21;935-948.*
Sonnenberg et al 1997 Infect Immun. 65(11): 4515-4524.*
Cole et al 1998 (Nature 393, 537-544).*
Rosenkrands 2000 Electrophoresis vol. 21, Issue 17, pp. 3740-3756.*
Kelkar et al Mol Cell Proteomics (2011) 10(12):M111.011627.*
Andersen P., Immunobiology. 1994; 191(4-5): 537-47.*
Andersen P., Scand. J. Immunol. 1997;.45(2):.115-31.*
Horwitz et al P.N.A.S. 1995; 92(5): 1530.*
Duijvesz, "Exosomes as Biomarker Treasure Chests for Prostate Cancer", European Urology: 59:823-831 (2011).
Giri, "Proteomic analysis identifies highly antigenic proteins on exosomes from M. tuberculosis-infected and culture filtrate protein-treated macrophages", Proteomics: 10(17): 3190-3202 (2010).
Keller, "Body fluid derived exosomes as a novel template for clinical diagnostics", Journal of Translational Medicine, 9:86:1-9 (2011).
Surinova, "On the Development of Plasma Protein Biomarkers", Journal of Proteome Research, 10:5-16 (2011).

* cited by examiner

*Primary Examiner* — Padma V Baskar
(74) *Attorney, Agent, or Firm* — Haukaas Fortius PLLC; Michael H. Haukaas

(57) ABSTRACT

The invention provides methods for the detection of *M. tuberculosis* proteins in or on exosomes derived from infected individuals. The methods can use a proteomic approach including mass spectroscopy, data mining and multiplex reaction monitoring to quickly examine a large amount of *M. tuberculosis* proteins to determine the best biomarkers for use in diagnostic tests to identify active TB patients.

11 Claims, 13 Drawing Sheets

| Rv Number | Protein Name | Day 14 | Day 28 | Day 56 | Day 112 |
|---|---|---|---|---|---|
| Rv0066c | isocitrate dehydrogenase | | | | + |
| Rv0125 | serine protease PepA | + | | | |
| Rv0129c | Antigen 85C | + | | + | |
| Rv0350 | DnaK | + | + | + | |
| Rv0363c | fructose-bisphosphate aldolase | | | | |
| Rv0440 | chaperonin GroEL | | | | |
| Rv0467 | isocitrate lyase | | | + | |
| Rv0934 | PstS1 | + | + | + | |
| Rv0969 | cation transporter P-type ATPase CtpV | + | | | |
| Rv1091 | PE-PGRS family protein | + | | | |
| Rv1178c | IpA | | | | |
| Rv1469 | cation transporter P-type ATPase CtpD | + | | | |
| Rv1827 | CFP17 | + | | | |
| Rv1837c | malate synthase G | + | | | + |
| Rv1860 | APA | + | + | + | |
| Rv1886c | Antigen 85B | + | + | + | + |
| Rv1908c | KatG | + | | | |
| Rv1926c | MPT63/MPB63 | + | | + | + |
| Rv1980c | MPT64/MPB64 | + | | + | + |
| Rv2031c | hspX | + | + | + | + |
| Rv2220 | GlnA1 | + | + | + | + |
| Rv2244 | acyl carrier protein | + | | | |
| Rv2376c | CFP2 | + | | | |
| Rv3097 | PE-PGRS family protein | | | | |
| Rv3418c | GroES | + | + | + | + |
| Rv3803c | MPT51/MPB51 | + | | + | |
| Rv3804c | Antigen 85a | + | + | + | |
| Rv3841 | BfrB | + | + | + | |

*Figure 3*

**Proteins Identified on Exosomes Released from Cultured Macrophages Infected with *M. tuberculosis***

<u>*M. tuberculosis* proteins</u>

1. Immunogenic proteins MPT63 and MPT64
2. Co-chaperonin GroES
3. KatG
4. Secreted MPT51
5. Antigen 85 Complex (A, B and C)
6. ESAT-6
7. APA/Fibronectin Attachment Protein
8. GlnA1

*Figure 4*

| | Macrophage[1] | Mouse[2] | Human |
|---|---|---|---|
| Rv0009\|ppiA | | | |
| Rv0066c\|icd2 | | x | |
| Rv0125\|pepA | | x | |
| Rv0129c\|Ag85c | x | x | |
| Rv0350\|DnaK | x | x | x |
| Rv0363c\|Fba | | x | |
| Rv0440\|groEL2 | | x | |
| Rv0934\|PstS1 | x | x | x |
| Rv1270c\|lprA | x | x | |
| Rv1469\|CtpD | | x | x |
| Rv1827\|GarA\|Cfp17 | x | x | |
| Rv1837c\|GlcB | x | x | x |
| Rv1860\|Apa\|Mpt32 | x | x | |
| Rv1886c\|Ag85b | x | x | |
| Rv1908c\|KatG | x | x | |
| Rv1926c\|Mpt63 | x | x | |
| Rv1932\|Cfp20\|Tpx | x | x | |
| Rv1980c\|Mpt64 | x | x | |
| Rv2031c\|HspX | x | x | x |
| Rv2220\|GlnA1 | x | x | |
| Rv2244\|AcpM | x | x | x |
| Rv2376c\|Cfp2 | x | x | |
| Rv2626c | | | x |
| Rv2780\|Ald | x | x | |
| Rv2878c\|Mpt53 | x | x | |
| Rv3248c\|SahH | x | x | |
| Rv3418c\|GroES | x | x | |
| Rv3441c\|MrsA | | | x |
| Rv3803c\|Mpt51\|fbpD | x | x | |
| Rv3804c\|Ag85a | x | x | |
| Rv3841\|BfrB | x | x | |
| Rv3874\|CFP10 | | | |
| Rv3875\|EsxA\|Esat6 | x | | |

*Figure 7*

| PTB compared to all TB- | | | | |
|---|---|---|---|---|
| Peptide | Sequence | SEQ ID | Protein | p-value |
| 33 | FALNAANAR | SEQ ID NO: 1 | GlcB | 0.0361 |
| 37 | SVFDDGLAFDGSSIR | SEQ ID NO: 2 | GlnA | 0.0478 |
| 61 | VYQNAGGTHPTTTYK | SEQ ID NO: 3 | Mpt64 | 0.0505 |
| 74 | EAPYELNITSATYQSAIPPR | SEQ ID NO: 4 | Mpt64 | 0.0428 |

| EPTB compared to all TB- | | | | |
|---|---|---|---|---|
| Peptide | Sequence | | Protein | p-value |
| 7 | PGLPVEYLQVPSPSMGR | SEQ ID NO: 5 | Ag85 | 0.0367 |
| 11 | VQFQGGGPHAVYLLDGLR | SEQ ID NO: 6 | Ag85c | 0.0164 |
| 12 | FLEGLTLR | SEQ ID NO: 7 | Ag85c | 0.0169 |
| 15 | LYASAEATDSK | SEQ ID NO: 8 | Mpt32 | 0.0054 |
| 33 | FALNAANAR | SEQ ID NO: 9 | GlcB | 0.0419 |
| 36 | ATIEQLLTIPLAK | SEQ ID NO: 10 | GlcB | 0.0297 |
| 46 | DGQLTIK | SEQ ID NO: 11 | HspX | 0.0006 |
| 47 | SEFAYGSFVR | SEQ ID NO: 12 | HspX | 0.0007 |
| 66 | TQDVAVLQLR | SEQ ID NO: 13 | PepA | 0.0106 |

SEQUENCE LISTING

```
<160> NUMBER OF SEQ ID NOS: 91

<210> SEQ ID NO 1
<211> LENGTH: 9
<212> TYPE: PRT
<213> ORGANISM: Mycobacterium tuberculosis

<400> SEQUENCE: 1

Phe Ala Leu Asn Ala Ala Asn Ala Arg
1               5

<210> SEQ ID NO 2
<211> LENGTH: 15
<212> TYPE: PRT
<213> ORGANISM: Mycobacterium tuberculosis

<400> SEQUENCE: 2

Ser Val Phe Asp Asp Gly Leu Ala Phe Asp Gly Ser Ser Ile Arg
1               5                   10                  15

<210> SEQ ID NO 3
<211> LENGTH: 15
<212> TYPE: PRT
<213> ORGANISM: Mycobacterium tuberculosis

<400> SEQUENCE: 3

Val Tyr Gln Asn Ala Gly Gly Thr His Pro Thr Thr Thr Tyr Lys
1               5                   10                  15

<210> SEQ ID NO 4
<211> LENGTH: 20
<212> TYPE: PRT
<213> ORGANISM: Mycobacterium tuberculosis

<400> SEQUENCE: 4

Glu Ala Pro Tyr Glu Leu Asn Ile Thr Ser Ala Thr Tyr Gln Ser Ala
1               5                   10                  15

Ile Pro Pro Arg
            20

<210> SEQ ID NO 5
<211> LENGTH: 17
<212> TYPE: PRT
<213> ORGANISM: Mycobacterium tuberculosis

<400> SEQUENCE: 5

Pro Gly Leu Pro Val Glu Tyr Leu Gln Val Pro Ser Pro Ser Met Gly
1               5                   10                  15

Arg
```

<210> SEQ ID NO 6
<211> LENGTH: 18
<212> TYPE: PRT
<213> ORGANISM: Mycobacterium tuberculosis

<400> SEQUENCE: 6

Val Gln Phe Gln Gly Gly Gly Pro His Ala Val Tyr Leu Leu Asp Gly
1 5 10 15

Leu Arg

<210> SEQ ID NO 7
<211> LENGTH: 8
<212> TYPE: PRT
<213> ORGANISM: Mycobacterium tuberculosis

<400> SEQUENCE: 7

Phe Leu Glu Gly Leu Thr Leu Arg
1 5

<210> SEQ ID NO 8
<211> LENGTH: 11
<212> TYPE: PRT
<213> ORGANISM: Mycobacterium tuberculosis

<400> SEQUENCE: 8

Leu Tyr Ala Ser Ala Glu Ala Thr Asp Ser Lys
1 5 10

<210> SEQ ID NO 9
<211> LENGTH: 9
<212> TYPE: PRT
<213> ORGANISM: Mycobacterium tuberculosis

<400> SEQUENCE: 9

Phe Ala Leu Asn Ala Ala Asn Ala Arg
1 5

<210> SEQ ID NO 10
<211> LENGTH: 13
<212> TYPE: PRT
<213> ORGANISM: Mycobacterium tuberculosis

<400> SEQUENCE: 10

Ala Thr Ile Glu Gln Leu Leu Thr Ile Pro Leu Ala Lys
1 5 10

<210> SEQ ID NO 11
<211> LENGTH: 7
<212> TYPE: PRT
<213> ORGANISM: Mycobacterium tuberculosis

<400> SEQUENCE: 11

Asp Gly Gln Leu Thr Ile Lys
1 5

<210> SEQ ID NO 12
<211> LENGTH: 10
<212> TYPE: PRT
<213> ORGANISM: Mycobacterium tuberculosis

<400> SEQUENCE: 12

Ser Glu Phe Ala Tyr Gly Ser Phe Val Arg
1 5 10

<210> SEQ ID NO 13
<211> LENGTH: 10
<212> TYPE: PRT
<213> ORGANISM: Mycobacterium tuberculosis

<400> SEQUENCE: 13

Thr Gln Asp Val Ala Val Leu Gln Leu Arg
1               5                   10

<210> SEQ ID NO 14
<211> LENGTH: 10
<212> TYPE: PRT
<213> ORGANISM: Mycobacterium tuberculosis

<400> SEQUENCE: 14

Ile Ala Leu Phe Gly Asn His Ala Pro Lys
1               5                   10

<210> SEQ ID NO 15
<211> LENGTH: 17
<212> TYPE: PRT
<213> ORGANISM: Mycobacterium tuberculosis

<400> SEQUENCE: 15

Val Ile Gln Gly Phe Met Ile Gln Gly Gly Asp Pro Thr Gly Thr Gly
1               5                   10                  15

Arg

<210> SEQ ID NO 16
<211> LENGTH: 22
<212> TYPE: PRT
<213> ORGANISM: Mycobacterium tuberculosis

<400> SEQUENCE: 16

Gly Ile Ser Asn Phe His Ser Pro Ser Asp Val Ile Val Asp Ala Ser
1               5                   10                  15

Met Pro Ala Met Ile Arg
            20

<210> SEQ ID NO 17
<211> LENGTH: 16
<212> TYPE: PRT
<213> ORGANISM: Mycobacterium tuberculosis

<400> SEQUENCE: 17

Leu Pro Asn Ile Ser Ala Ser Val Pro Gln Leu Val Ala Ala Ile Lys
1               5                   10                  15

<210> SEQ ID NO 18
<211> LENGTH: 10
<212> TYPE: PRT
<213> ORGANISM: Mycobacterium tuberculosis

<400> SEQUENCE: 18

Thr Gln Asp Val Ala Val Leu Gln Leu Arg
1               5                   10

<210> SEQ ID NO 19
<211> LENGTH: 10
<212> TYPE: PRT
<213> ORGANISM: Mycobacterium tuberculosis

<400> SEQUENCE: 19

Thr Gln Asp Val Ala Val Leu Gln Leu Arg
1               5                   10

<210> SEQ ID NO 20
<211> LENGTH: 8
<212> TYPE: PRT
<213> ORGANISM: Mycobacterium tuberculosis

<400> SEQUENCE: 20

Phe Leu Glu Gly Leu Thr Leu Arg
1               5

<210> SEQ ID NO 21
<211> LENGTH: 18
<212> TYPE: PRT
<213> ORGANISM: Mycobacterium tuberculosis

<400> SEQUENCE: 21

Val Gln Phe Gln Gly Gly Gly Pro His Ala Val Tyr Leu Leu Asp Gly
1               5                   10                  15

Leu Arg

<210> SEQ ID NO 22
<211> LENGTH: 10
<212> TYPE: PRT
<213> ORGANISM: Mycobacterium tuberculosis

<400> SEQUENCE: 22

Thr Thr Pro Ser Ile Val Ala Phe Ala Arg
1               5                   10

<210> SEQ ID NO 23
<211> LENGTH: 8
<212> TYPE: PRT
<213> ORGANISM: Mycobacterium tuberculosis

<400> SEQUENCE: 23

Ile Thr Gln Asp Leu Leu Asp Arg
1               5

<210> SEQ ID NO 24
<211> LENGTH: 10
<212> TYPE: PRT
<213> ORGANISM: Mycobacterium tuberculosis

<400> SEQUENCE: 24

Leu Tyr Thr Ser Pro Glu Asp Phe Glu Lys
1               5                   10

<210> SEQ ID NO 25
<211> LENGTH: 8
<212> TYPE: PRT
<213> ORGANISM: Mycobacterium tuberculosis

<400> SEQUENCE: 25

Ser Glu Ile Glu Glu Ala Leu Arg
1               5

<210> SEQ ID NO 26
<211> LENGTH: 16
<212> TYPE: PRT
<213> ORGANISM: Mycobacterium tuberculosis

<400> SEQUENCE: 26

Leu Arg Pro Asp Ile Leu Ala Gln Gly Gln Gln Val Ala Ala Lys
1               5                   10                  15

<210> SEQ ID NO 27
<211> LENGTH: 26
<212> TYPE: PRT
<213> ORGANISM: Mycobacterium tuberculosis

<400> SEQUENCE: 27

Ala Ala Val Glu Glu Gly Ile Val Ala Gly Gly Val Thr Leu Leu
1               5                   10                  15

Gln Ala Ala Pro Thr Leu Asp Glu Leu Lys
            20                  25

<210> SEQ ID NO 28
<211> LENGTH: 18
<212> TYPE: PRT
<213> ORGANISM: Mycobacterium tuberculosis

<400> SEQUENCE: 28

Ala Ser Phe Leu Asp Gln Val His Phe Gln Pro Leu Pro Pro Ala Val
1               5                   10                  15

Val Lys

<210> SEQ ID NO 29
<211> LENGTH: 32
<212> TYPE: PRT
<213> ORGANISM: Mycobacterium tuberculosis

<400> SEQUENCE: 29

Gly Leu Gly Glu Ala Gln Leu Gly Asn Ser Ser Gly Asn Phe Leu Leu
1               5                   10                  15

Pro Asp Ala Gln Ser Ile Gln Ala Ala Ala Gly Phe Ala Ser Lys
            20                  25                  30

<210> SEQ ID NO 30
<211> LENGTH: 16
<212> TYPE: PRT
<213> ORGANISM: Mycobacterium tuberculosis

<400> SEQUENCE: 30

Ser Asp Gly Ser Gly Asp Thr Phe Leu Phe Thr Gln Tyr Leu Ser Lys
1               5                   10                  15

<210> SEQ ID NO 31
<211> LENGTH: 17
<212> TYPE: PRT
<213> ORGANISM: Mycobacterium tuberculosis

<400> SEQUENCE: 31

Ile Thr Gly Asn Ser Ser Ala Asp Asp Ile Ala Thr Leu Ala Gly Ser
1               5                   10                  15

Arg

<210> SEQ ID NO 32
<211> LENGTH: 12
<212> TYPE: PRT
<213> ORGANISM: Mycobacterium tuberculosis

<400> SEQUENCE: 32

Val Val Ala Ala Ser Glu Leu Val Val Gly Asp Arg
1               5                   10

<210> SEQ ID NO 33
<211> LENGTH: 8
<212> TYPE: PRT
<213> ORGANISM: Mycobacterium tuberculosis

<400> SEQUENCE: 33

Leu Val Phe Leu Thr Gly Pro Lys
1               5

<210> SEQ ID NO 34
<211> LENGTH: 15
<212> TYPE: PRT
<213> ORGANISM: Mycobacterium tuberculosis

<400> SEQUENCE: 34

His Pro Asp Ser Asp Ile Phe Leu Asp Asp Val Thr Val Ser Arg
1               5                   10                  15

<210> SEQ ID NO 35
<211> LENGTH: 13
<212> TYPE: PRT
<213> ORGANISM: Mycobacterium tuberculosis

<400> SEQUENCE: 35

Ala Thr Ile Glu Gln Leu Leu Thr Ile Pro Leu Ala Lys
1               5                   10

<210> SEQ ID NO 36
<211> LENGTH: 15
<212> TYPE: PRT
<213> ORGANISM: Mycobacterium tuberculosis

<400> SEQUENCE: 36

Asn Tyr Thr Ala Pro Gly Gly Gly Gln Phe Thr Leu Pro Gly Arg
1               5                   10                  15

<210> SEQ ID NO 37
<211> LENGTH: 11
<212> TYPE: PRT
<213> ORGANISM: Mycobacterium tuberculosis

<400> SEQUENCE: 37

Val Val Phe Ile Asn Thr Gly Phe Leu Asp Arg
1               5                   10

<210> SEQ ID NO 38
<211> LENGTH: 9
<212> TYPE: PRT
<213> ORGANISM: Mycobacterium tuberculosis

<400> SEQUENCE: 38

Phe Ala Leu Asn Ala Ala Asn Ala Arg
1               5

<210> SEQ ID NO 39
<211> LENGTH: 19
<212> TYPE: PRT
<213> ORGANISM: Mycobacterium tuberculosis

<400> SEQUENCE: 39

Thr Thr Gly Asp Pro Pro Phe Pro Gly Gln Pro Pro Val Ala Asn
1               5                   10                  15

Asp Thr Arg

<210> SEQ ID NO 40
<211> LENGTH: 17
<212> TYPE: PRT
<213> ORGANISM: Mycobacterium tuberculosis

<400> SEQUENCE: 40

Pro Gly Leu Pro Val Glu Tyr Leu Gln Val Pro Ser Pro Ser Met Gly
1               5                   10                  15

Arg

<210> SEQ ID NO 41
<211> LENGTH: 17
<212> TYPE: PRT
<213> ORGANISM: Mycobacterium tuberculosis

<400> SEQUENCE: 41

Trp Glu Thr Phe Leu Thr Ser Glu Leu Pro Gln Trp Leu Ser Ala Asn
1               5                   10                  15

Arg

<210> SEQ ID NO 42
<211> LENGTH: 9
<212> TYPE: PRT
<213> ORGANISM: Mycobacterium tuberculosis

<400> SEQUENCE: 42

Asn Asp Pro Thr Gln Gln Ile Pro Lys
1               5

<210> SEQ ID NO 43
<211> LENGTH: 9
<212> TYPE: PRT
<213> ORGANISM: Mycobacterium tuberculosis

<400> SEQUENCE: 43

Glu Ala Thr Trp Leu Gly Asp Glu Arg
1               5

<210> SEQ ID NO 44
<211> LENGTH: 15
<212> TYPE: PRT
<213> ORGANISM: Mycobacterium tuberculosis

<400> SEQUENCE: 44

Phe Ala Pro Leu Asn Ser Trp Pro Asp Asn Ala Ser Leu Asp Lys
1               5                   10                  15

<210> SEQ ID NO 45
<211> LENGTH: 8
<212> TYPE: PRT
<213> ORGANISM: Mycobacterium tuberculosis

<400> SEQUENCE: 45

Thr Phe Gly Phe Gly Phe Gly Arg
1               5

<210> SEQ ID NO 46
<211> LENGTH: 13
<212> TYPE: PRT
<213> ORGANISM: Mycobacterium tuberculosis

<400> SEQUENCE: 46

```
Gly Ser Val Thr Pro Ala Val Ser Gln Phe Asn Ala Arg
1               5                   10
```

<210> SEQ ID NO 47
<211> LENGTH: 8
<212> TYPE: PRT
<213> ORGANISM: Mycobacterium tuberculosis

<400> SEQUENCE: 47

```
Thr Ala Asp Gly Ile Asn Tyr Arg
1               5
```

<210> SEQ ID NO 48
<211> LENGTH: 22
<212> TYPE: PRT
<213> ORGANISM: Mycobacterium tuberculosis

<400> SEQUENCE: 48

```
Asp Ser Phe Gly Glu Asp Tyr Gly Val Thr Ile Ala Asp Gly Pro Met
1               5                   10                  15

Ala Gly Leu Leu Ala Arg
            20
```

<210> SEQ ID NO 49
<211> LENGTH: 8
<212> TYPE: PRT
<213> ORGANISM: Mycobacterium tuberculosis

<400> SEQUENCE: 49

```
Gly Thr Gln Ala Val Val Leu Lys
1               5
```

<210> SEQ ID NO 50
<211> LENGTH: 15
<212> TYPE: PRT
<213> ORGANISM: Mycobacterium tuberculosis

<400> SEQUENCE: 50

```
Val Tyr Gln Asn Ala Gly Gly Thr His Pro Thr Thr Thr Tyr Lys
1               5                   10                  15
```

<210> SEQ ID NO 51
<211> LENGTH: 11
<212> TYPE: PRT
<213> ORGANISM: Mycobacterium tuberculosis

<400> SEQUENCE: 51

```
Phe Leu Ser Ala Ala Thr Ser Ser Thr Pro Arg
1               5                   10
```

<210> SEQ ID NO 52
<211> LENGTH: 9
<212> TYPE: PRT
<213> ORGANISM: Mycobacterium tuberculosis

<400> SEQUENCE: 52

```
Ala Phe Asp Trp Asp Gln Ala Tyr Arg
1               5
```

<210> SEQ ID NO 53
<211> LENGTH: 10
<212> TYPE: PRT
<213> ORGANISM: Mycobacterium tuberculosis

<400> SEQUENCE: 53

```
Ser Leu Glu Asn Tyr Ile Ala Gln Thr Arg
1               5                  10

<210> SEQ ID NO 54
<211> LENGTH: 20
<212> TYPE: PRT
<213> ORGANISM: Mycobacterium tuberculosis

<400> SEQUENCE: 54

Glu Ala Pro Tyr Glu Leu Asn Ile Thr Ser Ala Thr Tyr Gln Ser Ala
1               5                   10                  15

Ile Pro Pro Arg
            20

<210> SEQ ID NO 55
<211> LENGTH: 10
<212> TYPE: PRT
<213> ORGANISM: Mycobacterium tuberculosis

<400> SEQUENCE: 55

Ala Glu Leu Pro Gly Val Asp Pro Asp Lys
1               5                   10

<210> SEQ ID NO 56
<211> LENGTH: 7
<212> TYPE: PRT
<213> ORGANISM: Mycobacterium tuberculosis

<400> SEQUENCE: 56

Asp Gly Gln Leu Thr Ile Lys
1               5

<210> SEQ ID NO 57
<211> LENGTH: 14
<212> TYPE: PRT
<213> ORGANISM: Mycobacterium tuberculosis

<400> SEQUENCE: 57

Thr Val Ser Leu Pro Val Gly Ala Asp Glu Asp Ile Lys
1               5                   10

<210> SEQ ID NO 58
<211> LENGTH: 16
<212> TYPE: PRT
<213> ORGANISM: Mycobacterium tuberculosis

<400> SEQUENCE: 58

Gly Gly Tyr Phe Pro Val Ala Pro Asn Asp Gln Tyr Val Asp Leu Arg
1               5                   10                  15

<210> SEQ ID NO 59
<211> LENGTH: 9
<212> TYPE: PRT
<213> ORGANISM: Mycobacterium tuberculosis

<400> SEQUENCE: 59

Ile Pro Ile Thr Gly Ser Asn Pro Lys
1               5

<210> SEQ ID NO 60
<211> LENGTH: 16
<212> TYPE: PRT
<213> ORGANISM: Mycobacterium tuberculosis
```

```
<400> SEQUENCE: 60

Leu Val Pro Gly Tyr Glu Ala Pro Ile Asn Leu Val Tyr Ser Gln Arg
1               5                   10                  15

<210> SEQ ID NO 61
<211> LENGTH: 15
<212> TYPE: PRT
<213> ORGANISM: Mycobacterium tuberculosis

<400> SEQUENCE: 61

Ser Val Phe Asp Asp Gly Leu Ala Phe Asp Gly Ser Ser Ile Arg
1               5                   10                  15

<210> SEQ ID NO 62
<211> LENGTH: 15
<212> TYPE: PRT
<213> ORGANISM: Mycobacterium tuberculosis

<400> SEQUENCE: 62

Ile Glu Ser Glu Asn Pro Asp Ala Val Ala Asn Val Gln Ala Arg
1               5                   10                  15

<210> SEQ ID NO 63
<211> LENGTH: 13
<212> TYPE: PRT
<213> ORGANISM: Mycobacterium tuberculosis

<400> SEQUENCE: 63

Leu Glu Glu Glu Asn Pro Glu Ala Ala Gln Ala Leu Arg
1               5                   10

<210> SEQ ID NO 64
<211> LENGTH: 10
<212> TYPE: PRT
<213> ORGANISM: Mycobacterium tuberculosis

<400> SEQUENCE: 64

Ile Pro Asp Glu Asp Leu Ala Gly Leu Arg
1               5                   10

<210> SEQ ID NO 65
<211> LENGTH: 11
<212> TYPE: PRT
<213> ORGANISM: Mycobacterium tuberculosis

<400> SEQUENCE: 65

Thr Val Gly Asp Val Val Ala Tyr Ile Gln Lys
1               5                   10

<210> SEQ ID NO 66
<211> LENGTH: 14
<212> TYPE: PRT
<213> ORGANISM: Mycobacterium tuberculosis

<400> SEQUENCE: 66

Gly Ser Leu Val Glu Gly Gly Ile Gly Gly Thr Glu Ala Arg
1               5                   10

<210> SEQ ID NO 67
<211> LENGTH: 12
<212> TYPE: PRT
<213> ORGANISM: Mycobacterium tuberculosis

<400> SEQUENCE: 67
```

```
Ser Leu Ala Asp Pro Asn Val Ser Phe Ala Asn Lys
1               5                   10
```

<210> SEQ ID NO 68
<211> LENGTH: 25
<212> TYPE: PRT
<213> ORGANISM: Mycobacterium tuberculosis

<400> SEQUENCE: 68

```
Asp Ser Ile Tyr Tyr Val Asp Ala Asn Ala Ser Ile Gln Glu Met Leu
1               5                   10                  15

Asn Val Met Glu Glu His Gln Val Arg
            20                  25
```

<210> SEQ ID NO 69
<211> LENGTH: 18
<212> TYPE: PRT
<213> ORGANISM: Mycobacterium tuberculosis

<400> SEQUENCE: 69

```
Gly Leu Ala Ala Gly Leu Asp Pro Asn Thr Ala Thr Ala Gly Glu Leu
1               5                   10                  15

Ala Arg
```

<210> SEQ ID NO 70
<211> LENGTH: 13
<212> TYPE: PRT
<213> ORGANISM: Mycobacterium tuberculosis

<400> SEQUENCE: 70

```
Gly Leu Ser Thr His Glu Gly Ala Leu Leu Ser Glu Arg
1               5                   10
```

<210> SEQ ID NO 71
<211> LENGTH: 21
<212> TYPE: PRT
<213> ORGANISM: Mycobacterium tuberculosis

<400> SEQUENCE: 71

```
Leu Gln Phe Thr Ala Thr Thr Leu Ser Gly Ala Pro Phe Asp Gly Ala
1               5                   10                  15

Ser Leu Gln Gly Lys
            20
```

<210> SEQ ID NO 72
<211> LENGTH: 9
<212> TYPE: PRT
<213> ORGANISM: Mycobacterium tuberculosis

<400> SEQUENCE: 72

```
Glu Tyr Ala Glu Val Gln Pro Leu Lys
1               5
```

<210> SEQ ID NO 73
<211> LENGTH: 12
<212> TYPE: PRT
<213> ORGANISM: Mycobacterium tuberculosis

<400> SEQUENCE: 73

```
Gly Val Thr Glu Glu Thr Thr Thr Gly Val Leu Arg
1               5                   10
```

<210> SEQ ID NO 74

```
<211> LENGTH: 8
<212> TYPE: PRT
<213> ORGANISM: Mycobacterium tuberculosis

<400> SEQUENCE: 74

Asp Val Leu Ala Val Val Ser Lys
1               5

<210> SEQ ID NO 75
<211> LENGTH: 23
<212> TYPE: PRT
<213> ORGANISM: Mycobacterium tuberculosis

<400> SEQUENCE: 75

Ile Leu Val Gln Ala Asn Glu Ala Glu Thr Thr Ala Ser Gly Leu
1               5                   10                  15

Val Ile Pro Asp Thr Ala Lys
            20

<210> SEQ ID NO 76
<211> LENGTH: 16
<212> TYPE: PRT
<213> ORGANISM: Mycobacterium tuberculosis

<400> SEQUENCE: 76

Arg Ile Pro Leu Asp Val Ala Glu Gly Asp Thr Val Ile Tyr Ser Lys
1               5                   10                  15

<210> SEQ ID NO 77
<211> LENGTH: 13
<212> TYPE: PRT
<213> ORGANISM: Mycobacterium tuberculosis

<400> SEQUENCE: 77

Leu Ala Ala Thr Val Ala Asp Ala Val Ser Thr Ala Arg
1               5                   10

<210> SEQ ID NO 78
<211> LENGTH: 11
<212> TYPE: PRT
<213> ORGANISM: Mycobacterium tuberculosis

<400> SEQUENCE: 78

Val Ile Ala Ile Asn Ala Glu Pro Asn Gly Arg
1               5                   10

<210> SEQ ID NO 79
<211> LENGTH: 7
<212> TYPE: PRT
<213> ORGANISM: Mycobacterium tuberculosis

<400> SEQUENCE: 79

Tyr Val Leu Glu Glu Leu Arg
1               5

<210> SEQ ID NO 80
<211> LENGTH: 17
<212> TYPE: PRT
<213> ORGANISM: Mycobacterium tuberculosis

<400> SEQUENCE: 80

Trp His Asp Pro Trp Val His Ala Ser Leu Leu Ala Gln Asn Asn Thr
1               5                   10                  15

Arg
```

<210> SEQ ID NO 81
<211> LENGTH: 7
<212> TYPE: PRT
<213> ORGANISM: Mycobacterium tuberculosis

<400> SEQUENCE: 81

Phe Leu Glu Gly Phe Val Arg
1               5

<210> SEQ ID NO 82
<211> LENGTH: 9
<212> TYPE: PRT
<213> ORGANISM: Mycobacterium tuberculosis

<400> SEQUENCE: 82

Asn Asp Pro Leu Leu Asn Val Gly Lys
1               5

<210> SEQ ID NO 83
<211> LENGTH: 15
<212> TYPE: PRT
<213> ORGANISM: Mycobacterium tuberculosis

<400> SEQUENCE: 83

Ala Leu Gly Ala Thr Pro Asn Thr Gly Pro Ala Pro Gln Gly Ala
1               5                   10                  15

<210> SEQ ID NO 84
<211> LENGTH: 20
<212> TYPE: PRT
<213> ORGANISM: Mycobacterium tuberculosis

<400> SEQUENCE: 84

Val Gln Phe Gln Ser Gly Gly Ala Asn Ser Pro Ala Leu Tyr Leu Leu
1               5                   10                  15

Asp Gly Leu Arg
            20

<210> SEQ ID NO 85
<211> LENGTH: 14
<212> TYPE: PRT
<213> ORGANISM: Mycobacterium tuberculosis

<400> SEQUENCE: 85

Ala Gly Ala Asn Leu Phe Glu Leu Glu Asn Phe Val Ala Arg
1               5                   10

<210> SEQ ID NO 86
<211> LENGTH: 8
<212> TYPE: PRT
<213> ORGANISM: Mycobacterium tuberculosis

<400> SEQUENCE: 86

Thr Val Thr Asp Gln Val Gly Arg
1               5

<210> SEQ ID NO 87
<211> LENGTH: 11
<212> TYPE: PRT
<213> ORGANISM: Mycobacterium tuberculosis

<400> SEQUENCE: 87

Glu Ala Leu Ala Leu Ala Leu Asp Gln Glu Arg

-continued

```
1               5                   10

<210> SEQ ID NO 88
<211> LENGTH: 13
<212> TYPE: PRT
<213> ORGANISM: Mycobacterium tuberculosis

<400> SEQUENCE: 88

Gly Ala Ala Gly Thr Ala Ala Gln Ala Ala Val Val Arg
1               5                   10

<210> SEQ ID NO 89
<211> LENGTH: 11
<212> TYPE: PRT
<213> ORGANISM: Mycobacterium tuberculosis

<400> SEQUENCE: 89

Gln Glu Leu Asp Glu Ile Ser Thr Asn Ile Arg
1               5                   10

<210> SEQ ID NO 90
<211> LENGTH: 18
<212> TYPE: PRT
<213> ORGANISM: Mycobacterium tuberculosis

<400> SEQUENCE: 90

Thr Gln Ile Asp Gln Val Glu Ser Thr Ala Gly Ser Leu Gln Gly Gln
1               5                   10                  15

Trp Arg

<210> SEQ ID NO 91
<211> LENGTH: 17
<212> TYPE: PRT
<213> ORGANISM: Mycobacterium tuberculosis

<400> SEQUENCE: 91

Trp Asp Ala Thr Ala Thr Glu Leu Asn Asn Ala Leu Gln Asn Leu Ala
1               5                   10                  15

Arg
```

EXOSOMES AND DIAGNOSTIC BIOMARKERS

RELATED APPLICATIONS

This application claims priority under 35 U.S.C. §119(e) to U.S. Provisional Patent Application No. 61/795,220, filed Oct. 12, 2012, which is incorporated herein by reference.

GOVERNMENT SUPPORT

This invention was made with government support under Grant Nos. RO1-AI052438-01, RO1-AI056979-01 and HHSN266200400091C awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 6, 2013, is named 501.016US1_SL.txt and is 17,968 bytes in size.

BACKGROUND OF THE INVENTION

Tuberculosis (TB) is a common and often lethal infectious disease caused by the *Mycobacterium* genus of bacteria, typically *Mycobacterium tuberculosis* (Mtb). Mtb is air transmissible and easily spreads between individuals through respiratory fluid droplets. Most Mtb infections are asymptomatic, latent TB infections (LTBI), however, some of these infections can eventually progress to active TB infections. TB typically infects the pulmonary system of an afflicted individual; however, the disease can also spread through the body causing extrapulmonary TB (EPTB). Left untreated, active TB typically kills more than half the individuals it affects.

It is estimated that one third of the entire global population is currently infected with Mtb. In 2007 alone, there were an estimated 8 million new cases of TB. During the same year, there were an estimated 1.7 million deaths attributed to TB. Active TB is particularly common in low to middle-income countries, accounting for roughly 80% of reported disease cases. Furthermore, the high prevalence of HIV in areas such as sub-Saharan Africa greatly adds to TB's lethality.

Given TB's high prevalence and associated deaths, fast diagnosis and treatment of active TB is of paramount importance. Currently, the two most common methods of detecting Mtb infection are the sputum acid-fast bacilli smear microscopy test (AFB) and the tuberculin skin test (TST).

In AFB smears, sputum is collected from patients and the sample is examined microscopically after a bacterial staining procedure. Although AFB can produce presumptive results in a few hours, it suffers from poor sensitivity. AFB also fails to identify TB patients having little to no Mtb in their sputum or those patients who are unable to produce sputum. This is especially common in young children or HIV infected patients. Further, Mtb replicates slowly, making positive identification of Mtb in cultures lengthy, ranging from days to weeks.

TST is a composite measure of cell-mediated immunity in response to TB antigen (PPD) stimulation, which is injected under the skin of a patient. However, it may take 2 to 3 days before the results can be obtained and frequently delivers false positive or false negative results. Also, this test does not distinguish latent infection from active disease, which is important in a diagnostic setting.

In addition, nucleic acid amplification tests and interferon-gamma based tests have been developed. Although these tests can provide for rapid detection of Mtb, they also suffer from lack of sensitivity and specificity in certain situations. Moreover, both the cost of such tests, as well as the required expertise to perform such tests can be prohibitive.

A critical need exists for novel diagnostic and prognostic assays to identify those at risk for TB and capable of transmitting Mtb to other individuals. The detection of Mtb biomarkers in a patient's bodily fluid (blood, urine, etc.) provides such an opportunity. Exosomes contained within these bodily fluids can serve as an excellent source of Mtb biomarkers.

Therefore, the identification of specific and easily measured exosomal Mtb biomarkers will have a significant impact on global TB diagnosis and treatment. However, due to the complexity of TB disease, identifying a single Mtb biomarker with the required sensitivity and specificity has been a challenge. Here, the applicants disclose a method of identifying new exosomal Mtb biomarkers indicative of disease and using these exosomal Mtb biomarkers in a robust, simple, accurate and cost effective bioassay to diagnose individuals with active TB disease.

SUMMARY

The invention provides for a method of detecting exosomal Mtb biomarkers and a method for using the detected exosomal Mtb biomarkers to diagnose patients with active TB infections.

Accordingly, one embodiment of the invention involves a method of identifying proteins diagnostic of an active Mtb infection comprising:

(a) providing a sample from at least one subject known to have an Mtb infection;
(b) analyzing the at least one sample to identify proteins in the sample;
(c) the proteins or fragments thereof being located on or in exosomes in the sample;

wherein the proteins comprised by the sample may be diagnostic of an active Mtb infection.

In another embodiment, the proteins from the sample of the at least one subject is fractionated and digest.

In another embodiment, the proteins are compared across samples.

In another embodiment, the proteins compared across samples allow for the identification of a protein signature associated with an active Mtb infection.

In another embodiment, identifying the proteins associated with the active Mtb infection is done by mass spectroscopy.

In another embodiment, the sample is taken from a bodily fluid such as blood, urine or serum.

In another embodiment, the exosomes are concentrated prior analyzing the proteins.

In another embodiment, the method includes identifying proteins diagnostic of an Mtb infection wherein the proteins identify a protein signature indicative of active Mtb infection.

In another embodiment, the protein signature comprises at least one protein selected from the group consisting of Rv0066c, Rv0125, Rv0129c, Rv0350, Rv0363c, Rv0440, Rv0467, Rv0934, Rv0969, Rv1091, Rv1270c, Rv1469, Rv1827, Rv1837c, Rv1860, Rv1886c, Rv1908c, Rv1926c, Rv1980c, Rv2031c, Rv2220, Rv2244, Rv2376c, Rv2626c, Rv3388, Rv3418c, Rv3441c, Rv3803c, Rv3804c, Rv3841 and Rv3874.

In yet another embodiment, the protein signature comprises at least one protein selected from the group consisting of Rv0009c, Rv0066c, Rv0125, Rv0129c, Rv0350, Rv0363c, Rv0440, Rv0467, Rv0934, Rv1270c, Rv1469, Rv1827, Rv1837c, Rv1860, Rv1886c, Rv1908c, Rv1926c, Rv1932, Rv1980c, Rv2031c, Rv2220, Rv2244, Rv2376c, Rv2626c, Rv2780, Rv2878c, Rv3248c, Rv3388, Rv3418c, Rv3441c, Rv3803c, Rv3804c, Rv3841, Rv3874, and Rv3875.

In another embodiment, the invention involves a method of detecting an active Mtb infection comprising:
(a) providing a sample from at least one subject having an active Mtb infection;
(b) providing at least one means to detect at least one protein or fragment thereof with an active Mtb infection;
(c) the proteins or fragments thereof being located on or in exosomes in the sample;
(d) detecting proteins or fragments thereof associated with an active Mtb infection comprised by the sample;
wherein, if the proteins associated with an active Mtb infection are detected in the sample, the subject has an active Mtb infection.

In a further embodiment, at least one protein or fragment thereof associated with an active Mtb infection is selected from the group consisting of Rv0066c, Rv0125, Rv0129c, Rv0350, Rv0363c, Rv0440, Rv0467, Rv0934, Rv0969, Rv1091, Rv1270c, Rv1469, Rv1827, Rv1837c, Rv1860, Rv1886c, Rv1908c, Rv1926c, Rv1980c, Rv2031c, Rv2220, Rv2244, Rv2376c, Rv2626c, Rv3388, Rv3418c, Rv3441c, Rv3803c, Rv3804c, Rv3841 and Rv3874.

In yet further embodiments, at least one protein or fragment thereof associated with an active Mtb infection comprises at least one protein from the group consisting of Rv0009c, Rv0066c, Rv0125, Rv0129c, Rv0350, Rv0363c, Rv0440, Rv0467, Rv0934, Rv1270c, Rv1469, Rv1827, Rv1837c, Rv1860, Rv1886c, Rv1908c, Rv1926c, Rv1932, Rv1980c, Rv2031c, Rv2220, Rv2244, Rv2376c, Rv2626c, Rv2780, Rv2878c, Rv3248c, Rv3388, Rv3418c, Rv3441c, Rv3803c, Rv3804c, Rv3841, Rv3874, and Rv3875.

In another embodiment, the at least one means of detecting the at least one protein or fragment thereof comprises an antibody.

In another embodiment, the at least one protein or fragment thereof is immobilized on a solid support or is performed on an ELISA, Dipstick assay, microfluidic device or micro array.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3. An example of identified dominant exosomal proteins isolated from Mtb-infected mice.

FIG. 4. An example of identified exosomal proteins released from cultured macrophages infected with Mtb.

FIG. 7. Mycobacterial Proteins (with respective RV# annotations) included in a final MRM assays. Proteins were identified during the LC-MS/MS discovery phase, from exosomes isolated from Mtbb-infectedJ774a.1 murine macrophage cell line, broncheoalveolar lavage fluid from Mtb-infected BALB/c mice or serum from patients diagnosed with active tuberculosis.

FIG. 8. An example of using the herein disclosed method of identifying exosomal TB biomarkers to differentiate between types of infection. T-tests were performed to compare each peptide in PTB and EPTB versus TB samples. Those peptides (SEQ ID NOS: 1-13) listed in this table were found to contribute significantly with categorization in either PTB or EPTB category.

DETAILED DESCRIPTION

Figure 1:
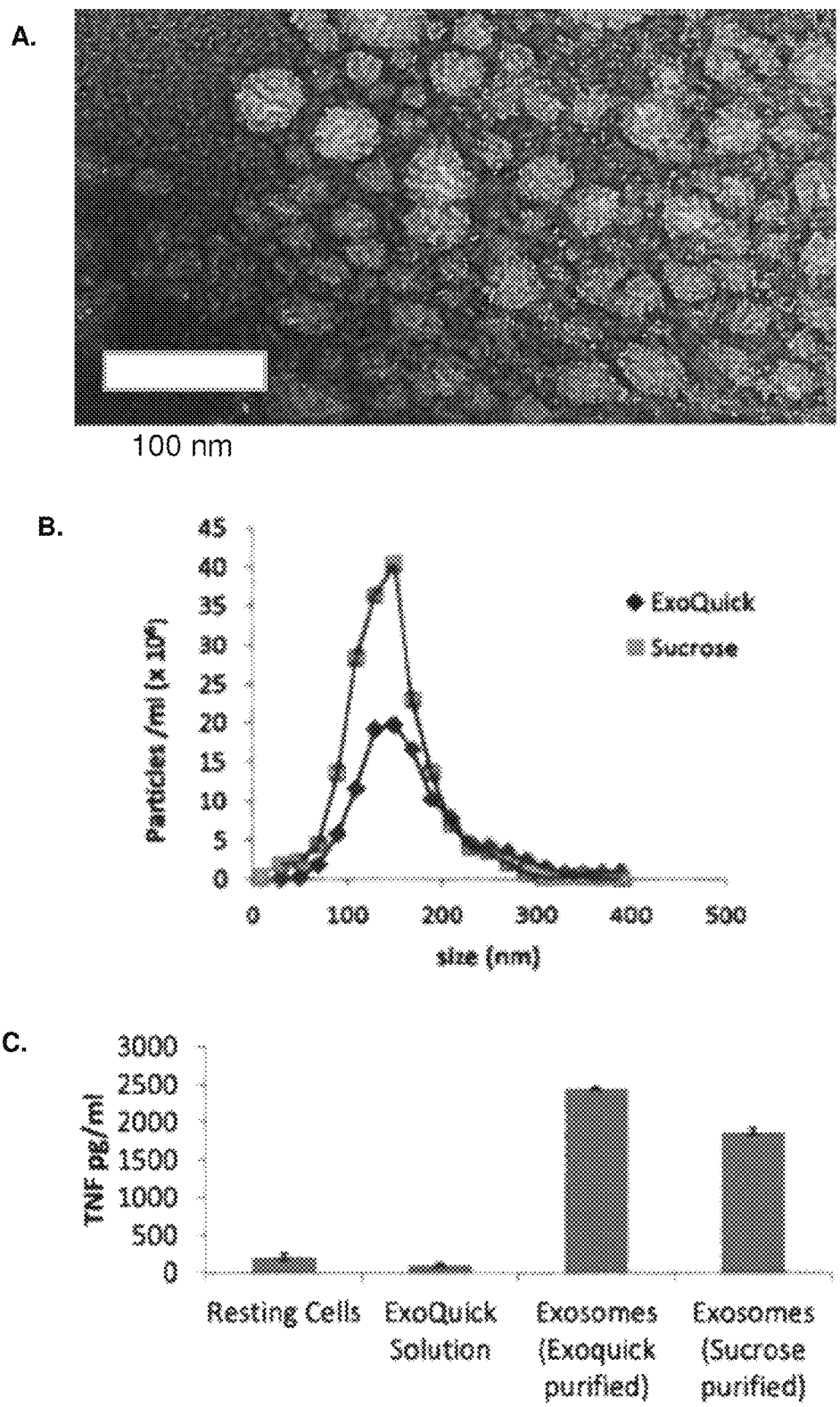
FIG. 1. (A) Morphological characterization of human serum derived exosomes by TEM. Exosomes purified from serum using ExoQuick™ were suspended in 155 mM Ammonium bicarbonate and mounted on a carbon-formvar-coated copper grid. Grids were stained with 2% uranyl acetate. Scale bar=100 nm. A comparison of Exoquick™ and sucrose gradient purified exosomes shows similar (B) recovery and (C) bioactivity of purified exosomes.

*Mycobacterium tuberculosis* (Mtb) is the primary causative agent of tuberculosis (TB). Mtb currently infects one third of the world's population, many who will go on to develop active TB disease. Active TB is responsible for between 1.5-2 million deaths per year. Although diagnostic tests are available for detecting patients with TB, many of these tests suffer from poor sensitivity and specificity. Moreover, many areas of the globe hardest hit by TB are impoverished, lacking both the funds to purchase TB diagnostic equipment and to train the personnel required to use such equipment.

Accordingly, what are needed are a new method of TB biomarker discovery and the use of these biomarkers in a simple, low cost, rapid and accurate method for TB diagnosis outside the clinical lab setting.

Disclosed herein is a novel approach to TB diagnostics based on biomarkers present on or in exosomes released from Mtb infected host cells into bodily fluids.

An exosome based approach for identification of TB infection has several advantages over current methods of detecting active TB in patients: 1) exosomes are readily found in bodily fluid, 2) can be readily purified, and 3) are known to capture and concentrate various biomolecules to an extent making detection and identification easier.

Exosomes

Exosomes are small membrane bound vesicles that are released into the extracellular environment from a variety of different cells such as but not limited to, cells that originate from, or are derived from, the ectoderm, endoderm, or mesoderm including any such cells that have undergone genetic, environmental, and/or any other variations or alterations (e.g. bacterial/virally infected cells, tumor cells or cells with genetic mutations). An exosome is typically created intracellularly when a segment of the cell membrane spontaneously invaginates and is ultimately exocytosed.

Exosomes can have, but not be limited to, a diameter of greater than about 10, 20, or nm. They can have a diameter of about 30-1000 nm, about 30-800 nm, about 30-200 nm, about 30-100 nm, about 20 nm to about 100 nm, about 30 nm to about 150 nm, about 30 nm to about 120 nm, about 50 nm to about 150 nm, or about 50 nm to about 120 nm. In some embodiments, the exosomes can have, but not be limited to, a diameter of at least 20 nm and less than about 1000 nm, 800 nm, 500 nm, 200 nm, 100 nm, or 50 nm. As used throughout, the term "about," when referring to a value or to an amount is meant to encompass variations in some embodiments±10% from the specified amount, as such variations are appropriate.

Exosomes may also be referred to as microvesicles, nanovesicles, vesicles, dexosomes, bleb, blebby, prostasomes, microparticles, intralumenal vesicles, endosomal-like vesicles or exocytosed vehicles. As used herein, exosomes can also include any shed membrane bound particle that is derived from either the plasma membrane or an internal membrane. Exosomes can also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen, including but not limited to tumor-derived microRNAs or intracellular proteins. Blebs and blebbing are further described in Charras et al, *Nature Reviews Molecular and Cell Biology*, Vol. 9, No. 11, p. 730-736 (2008). Exosomes can also include membrane fragments.

Isolation of Exosomes

Exosomes can be directly assayed from the biological samples, such that the level of exosomes is determined or the one or more biomarkers of the exosomes are determined without prior isolation, purification, or concentration of the exosomes.

Alternatively, in some embodiments, an exosome may be purified or concentrated prior to analysis. Analysis of an exosome can include quantitating the amount of one or more exosome populations of a biological sample. For example, a heterogeneous population of exosomes can be quantitated, or a homogeneous population of exosomes, such as a population of exosomes with a particular biomarker profile, or derived from a particular cell type (cell-of-origin specific exosomes) can be isolated from a heterogeneous population of exosomes and quantitated. Analysis of an exosome can also include detecting, quantitatively or qualitatively, a particular biomarker profile or a bio-signature, of an exosome. An enriched population of exosomes can be obtained from a biological sample derived from any cell or cells capable of producing and releasing exosomes into the bodily fluid.

In a preferred embodiment, the biological sample of an individual with active TB is taken from the blood, plasma or urine. One skilled in the art will recognize that a biological sample can also be taken from, but not limited to the following bodily fluids: peripheral blood, ascites, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation that may be of fetal or maternal origin. The biological sample may also be a tissue sample or biopsy, from which exosomes may be obtained.

Exosomes may be concentrated or isolated from a biological sample using size exclusion chromatography, density gradient centrifugation, differential centrifugation, nanomembrane ultrafiltration, immunoabsorbent capture, affinity purification, microfluidic separation, commercially available protein purification kits, or combinations thereof.

Size exclusion chromatography, such as gel permeation columns, centrifugation or density gradient centrifugation, and filtration methods can be used. For example, exosomes can be isolated by differential centrifugation, anion exchange and/or gel permeation chromatography, sucrose density gradients, organelle electrophoresis, magnetic activated cell sorting (MACS), or with a nanomembrane ultrafiltration concentrator. Various combinations of isolation or concentration methods can be used.

Highly abundant proteins, such as albumin and immunoglobulin, may hinder isolation of exosomes from a biological sample. For example, exosomes may be isolated from a biological sample using a system that utilizes multiple antibodies that are specific to the most abundant proteins found in blood. Such a system can remove up to several proteins at once, thus unveiling the lower abundance species such as cell-of-origin specific exosomes.

This type of system can be used for isolation of exosomes from biological samples such as blood, cerebrospinal fluid, urine and/or saliva. The isolation of exosomes from a biological sample may also be enhanced by high abundant protein removal methods as described in Chromy et al. J. Proteome Res 2004; 3: 1120-1127. In another embodiment, the isolation of exosomes from a biological sample may also be enhanced by removing serum proteins using glycopeptide capture as described in Zhang et al, Mol Cell Proteomics 2005; 4: 144-155. In addition, exosomes from a biological sample such as urine may be isolated by differential centrifugation followed by contact with antibodies directed to cytoplasmic or anti-cytoplasmic epitopes as described in Pisitkun et al., Proc Natl Acad Sci USA, 2004; 101: 13368-13373.

In a preferred embodiment, a commercially available protein isolation kit can be used for exosomal isolation, for example ExoQuick™ (System Biosciences). Commercially available protein isolation kits are advantages because they are relatively quick, low cost and typically present a high yield of protein for analysis. The presence of exosomes can be confirmed by detecting known exosomal markers such as, but not limited to MHC Class I protein, LAMP1, CD9, CD63 and CD81 via western blotting or other mean s of detection.

Figure 2:
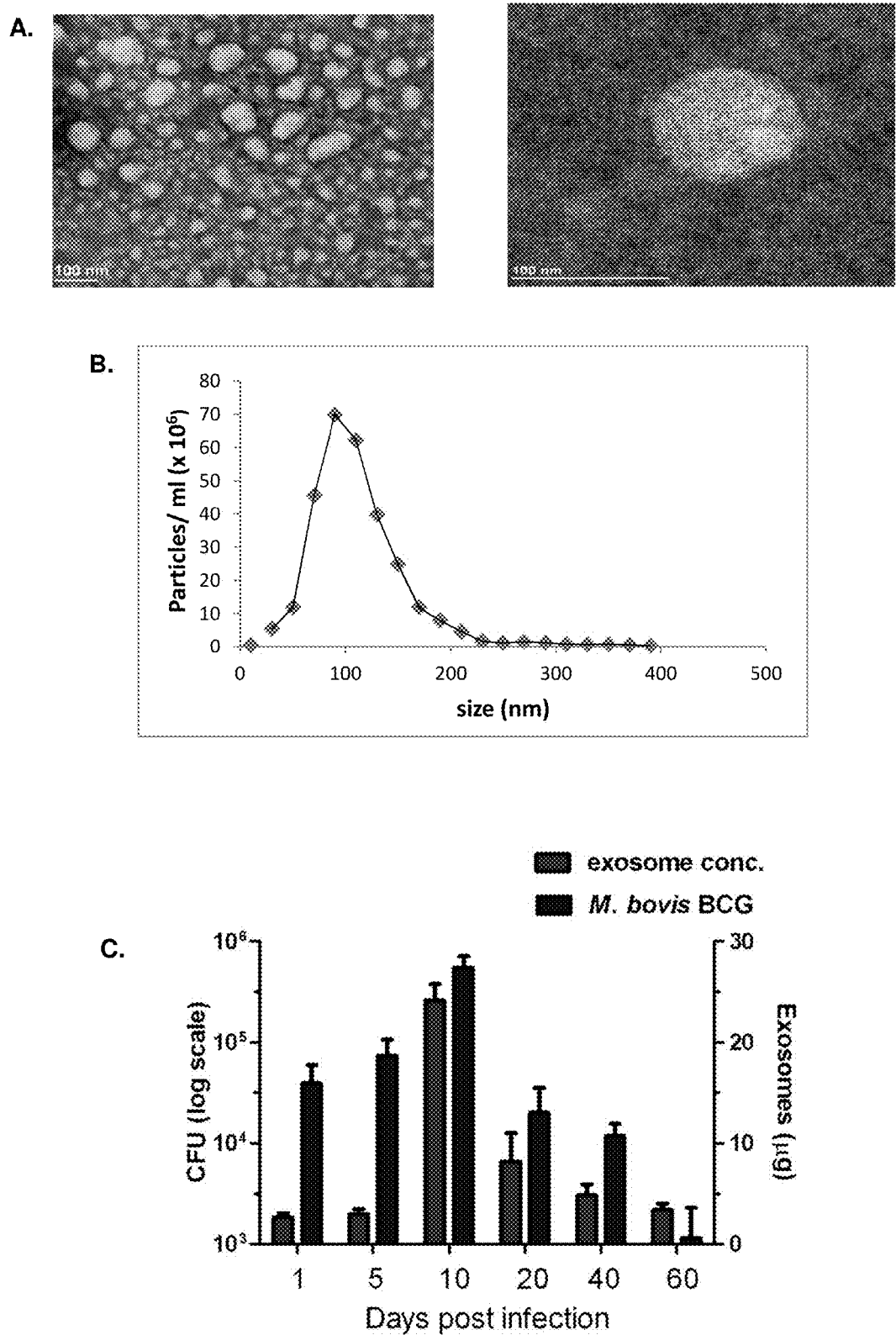
FIG. 2. (A) Two TEM images of human serum derived exosomes. Scale bar=100 nm. Exosomal concentration corresponds to bacterial load: (B) a graph of concentration vs. particle size; (C) a graph of cell forming units (CFU) vs. days post infection (for each day: left bar=exosome concentration; right bar=*M. bovis* BCG).

Transmission Electron Microscopy (TEM), protein concentration, and Nano-Sight LM-10HS analysis can also be used to analyze the presence and purity of isolated exosomes. Moreover, kits such as ExoQuick™ have shown good yield of exosomes from bodily fluid. FIG. 1 shows a comparison of exosomes isolated using the ExoQuick™ method as compared to sucrose gradient exosomal purification. Moreover, not only did ExoQuick™ have a superior yield of exosomes, but the bioactivity of selected proteins remained similar. Moreover, the applicants show that the exosomal burden reflects the bacterial load (see FIG. 2).

Mtb Biomarkers in Exosomes

Generally speaking, a biomarker is anything that can be used as an indicator of a biological state of an organism, most commonly a disease state. Biomarkers are typically, but not limited to nucleic acid (e.g. RNA or DNA), protein, peptide, polypeptide, antigen, lipid, carbohydrate, or proteoglycan. Protein biomarkers may also have other characteristics such as truncations, mutations, various expression level (such as overexpression or underexpression as compared to a reference level), and post-translational modifications.

More specifically, exosomes shed from Mtb infected cells are known to concentrate specific Mtb proteins or fragments thereof in or on the surface of the exosome. Therefore, exosomes serve as an excellent source of biomarker determinates. Typically, the source of exosomal biomarkers are collected from a biological sample (e.g. bodily fluid) taken from an individual suspected of Mtb infection. However, is some instances, it may be beneficial to collect exosomal biomarkers from other sources. For example, exosomes may be collected from biopsied tissue samples, non-human sources (e.g. other mammals) or various cell lines used in medical research. One such cell line is mouse macrophage cell line J774a. A person skilled in the art will recognize that many different animal models and cell lines exist that are specific to a research need and are within the scope of this disclosure. FIGS. 3 and 4 provide examples of Mtb proteins found in or on exosomes in infected mice and macrophages, respectively.

Detection of Exosomal Mtb Biomarkers

Detection of exosomal TB biomarkers can be done by a number of methods. These include, but are not limited to: western blotting, binding assays, flow cytometry and mass spectrometry.

In one embodiment, the applicants use mass spectrometry (MS) to identify exosomal TB biomarkers. MS is a powerful tool for the detection of exosomal TB biomarkers. MS is advantages because it does not require antibodies, which are, many times, not readily available for various proteins. MS also only requires a small sample size, has high specificity and sensitivity and has high throughput capability.

Without being bound by theory, an MS analysis produces a record of the masses of the atoms or molecules in a sample material. MS ionizes chemical or biological compounds to produce charged fragments, (ions) which are then separated by their resulting mass-to-charge ratio.

Generally, MS has three parts: an ion source, a mass analyzer and a detector. The ionizer converts the sample or a portion thereof into ions. Many different ionization techniques exist and can be adapted to the type of sample (e.g. phase of the sample) and the efficiency of ionization of the sample. Types of ionization include, but are not limited to electronic ionization, chemical ionization, electrospray ionization, matrix assisted deabsorption/ionization (MALDI), inductive coupling plasma sources, spark ionization and thermal ionization (TIMS).

The ions are then sent to a mass analyzer. The mass analyzer generally contains an electric and magnetic field that interact with the ionized sample. The speed and direction of the ions is affected by the mass-to-charge ration as they interact with the electric and magnetic fields. Types of mass analyzers can include, but are not limited to sector field, time-of-flight (TOF) quadrupole mass analyzer/filter, quadrupole trap, and Fourier transform mass spectroscopy (FTMS).

The spectrum of ions is then collected by the detector, which records the abundance of each type of ion and gives a mass spectrum analysis to the end user. Types of detectors include, but are not limited to tandem mass spectroscopy, gas chromatography mass spectroscopy (GC-MS), liquid chromatography mass spectroscopy (LC-MS), and ion mobility mass spectroscopy.

Exosomal TB Biomarker Discovery

Figure 5:
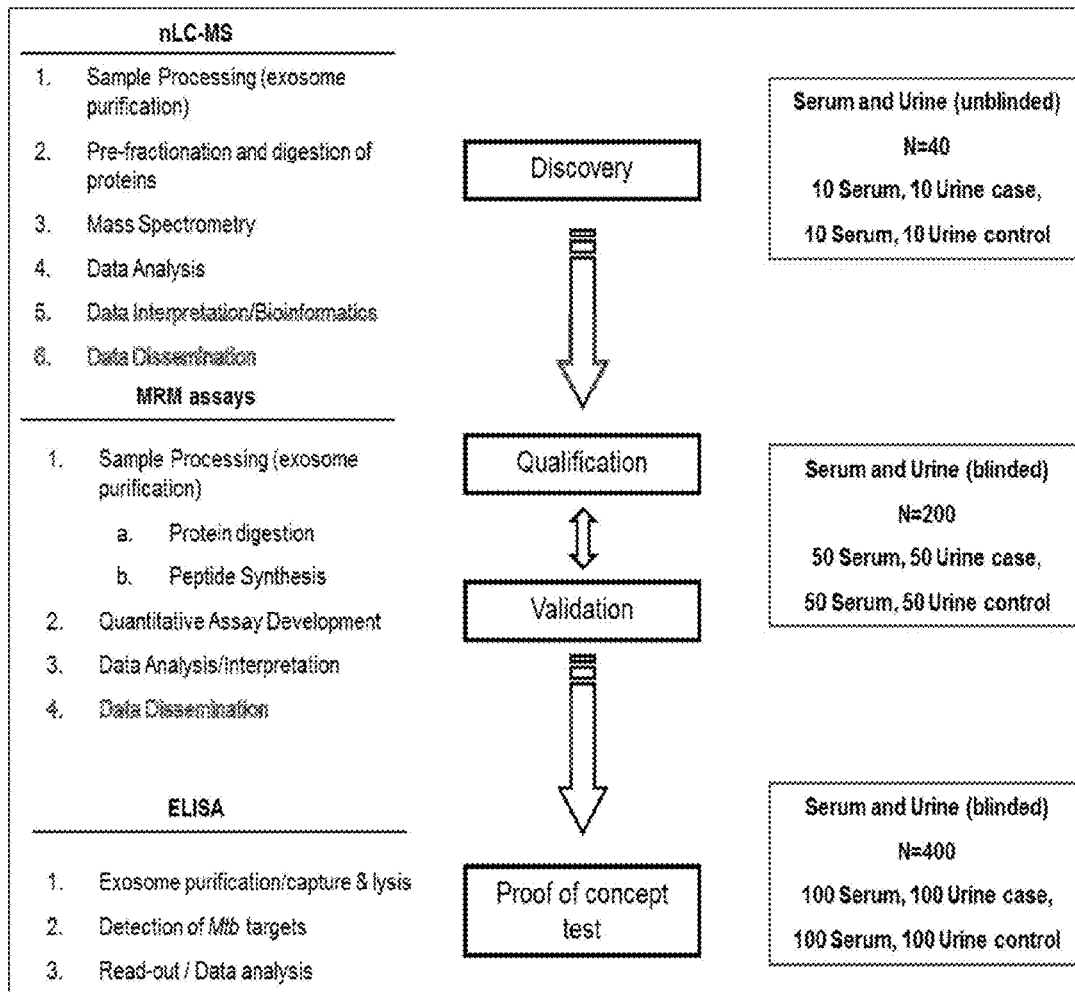
FIG. 5. An example of a three-phase proteomics workflow to identify and validate new Mtb biomarkers.
Figure 6:
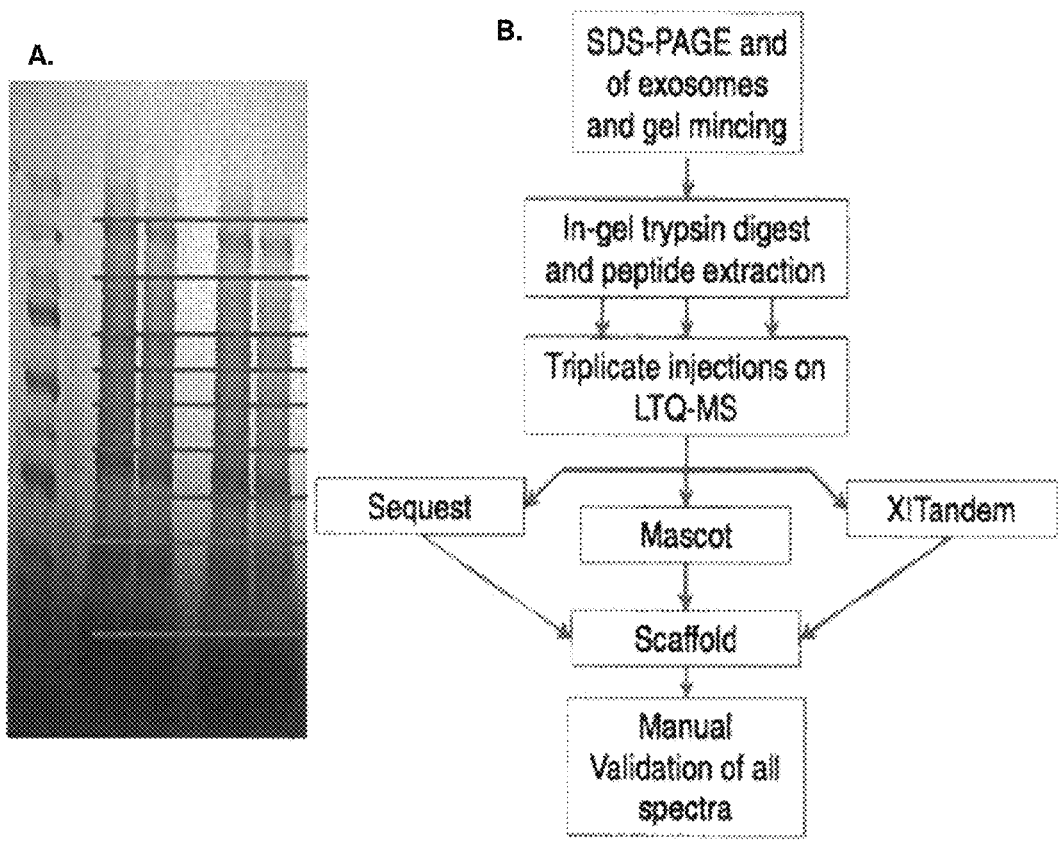
FIG. 6. (A) Illustration of an exosome-containing gel. (B) An example of a discovery phase of a three-phased proteomics workflow.

In a preferred embodiment of the invention, a three-phase proteomics workflow is used to identify potential Mtb biomarkers. A three-phase proteomics workflow includes 1) a discovery phase, 2) a qualification/validation phase, and 3) a proof of concept test phase. An example of a three-phase proteomics workflow is shown in FIG. 5. One skilled in the art will recognize that a proteomics workflow could have more or less steps depending on need.

Discovery Phase

The discovery phase, in some embodiments, involves several steps including but not limited to: a) sample processing, b) pre-mass spectroscopy fractionation and digestion of proteins, c) mass spectroscopy, d) data analysis, e) data interpretation and bioinformatics, and f) data dissemination.

Sample processing involves the identification of exosomes from Mtb infected bodily fluid. Exosomes can also be isolated from animal models and cell lines infected with Mtb. The exosomes can be purified using any method described previously (e.g. Exoquick™, sucrose gradient centrifugation).

Purified exosomes can then be subjected to polyacrylamide gel electrophoresis (PAGE) to fractionate the exosomal sample. PAGE can be multi-dimensional depending on the need of the end user. The fractionated exosomal samples can then be subjected to digestion via a protease enzyme. Protease enzymes can include serine proteases, threonine proteases, cysteine proteases, aspartate proteases, glutamic proteases, and metallo-proteases or a mixture thereof. In a preferred embodiment, the serine protease trypsin is used to digest the exosomal proteins. Digestion of the proteins can occur while the proteins are immobilized in the polyacrylamide gel, or in an in-solution digest, or the protein bands can be excised and then the proteins are digested.

In a preferred embodiment, the digested proteins are subject to nano-liquid chromatography-Mass spectroscopy (nLC-MS). One skilled in the art will recognize any form of mass spectroscopy can be used in place of nLC-MS as described above.

The nLC-MS data can then be filtered to eliminate false positive discoveries by examining the Mtb CDC1551 and H37Rv genomes and compared to the human genome. A multiplicity of samples (e.g. 2, 3, 4, etc.) can be analyzed as well to further eliminate false positive discoveries.

After removal of false positive discoveries, the data from the samples can be loaded into a proteomics software program (e.g. Spectrum or Scaffold) to determine the identity of potential Mtb biomarkers. These programs allow for filtering to validate protein identities based on various filter parameters including, but not limited to mass tolerance, number of proteins/peptides, protein probability and peptide probability. A random amount of identities can be manually validated for identity, where the results of the manual validation can be used to increase the stringency of the filter parameters.

Lastly, a scoring system can be used to determine the proteins with the most unique peptides. Those proteins with the highest amount of unique peptides can be good candidate exosomal Mtb biomarkers to proceed to the qualification/validation portion of the three-phase proteomics workflow.

The discovery phase will identify a battery of candidate proteins that will require qualification using a distinct method over the one used in the discovery phase. In a preferred embodiment of the invention, multiple reaction monitoring (MRM) mass spectroscopy can used for this validation step.

Qualification and Validation Phase

MRM assays employ a highly sensitive mass spectroscopy based method typically, but not limited to, using triple quadrupole mass spectrometer. MRM assays require prior identification of peptides or proteins of interest. The identification of potential biomarker candidate proteins is generated during the discovery phase, such as the one described above. The high sensitivity and specificity of the triple quadrupole MS, coupled with a combination of unique precursor/transition ion pairs can confidently identify a target protein in the femtomolar/attomolar quantities. Moreover, not only can MRM assays identify dozens of proteins or peptides in a single sample, MRM assays do not rely on an antibody for validation, where many times an antibody is not available for the protein requiring validation.

MRM assays proceed by the analysis of a list of peptides obtained for each protein identified in the discovery phase. The collected data (detected MS fragment ions, LC retention times, and molecular weight etc.) can be loaded to any number of available MRM software programs such as Skyline. These programs generate a list of peptide surrogates focusing on required parameters such as sensitivity, precision, selectivity, stability, and LC retention times. Optimally, several peptide surrogates for each candidate protein will be selected for verification. Optimally, a subset of these surrogates will have an identical synthetic peptide with a stable isotope contained therein that will allow use as an internal standard. Accordingly, these internal standards can be used to create and validate a quantitative assay for the peptide surrogates of the candidate proteins.

After the experimental conditions have been optimized, isolated exosomes from Mtb infected samples are digested with a protease (e.g. trypsin). A known quantity of synthetic peptide is added to the sample as an internal standard. The samples are then analyzed via the newly created MRM assay to yield a highly accurate quantification of the protein corresponding to the synthetic surrogate peptide.

Figure 10:
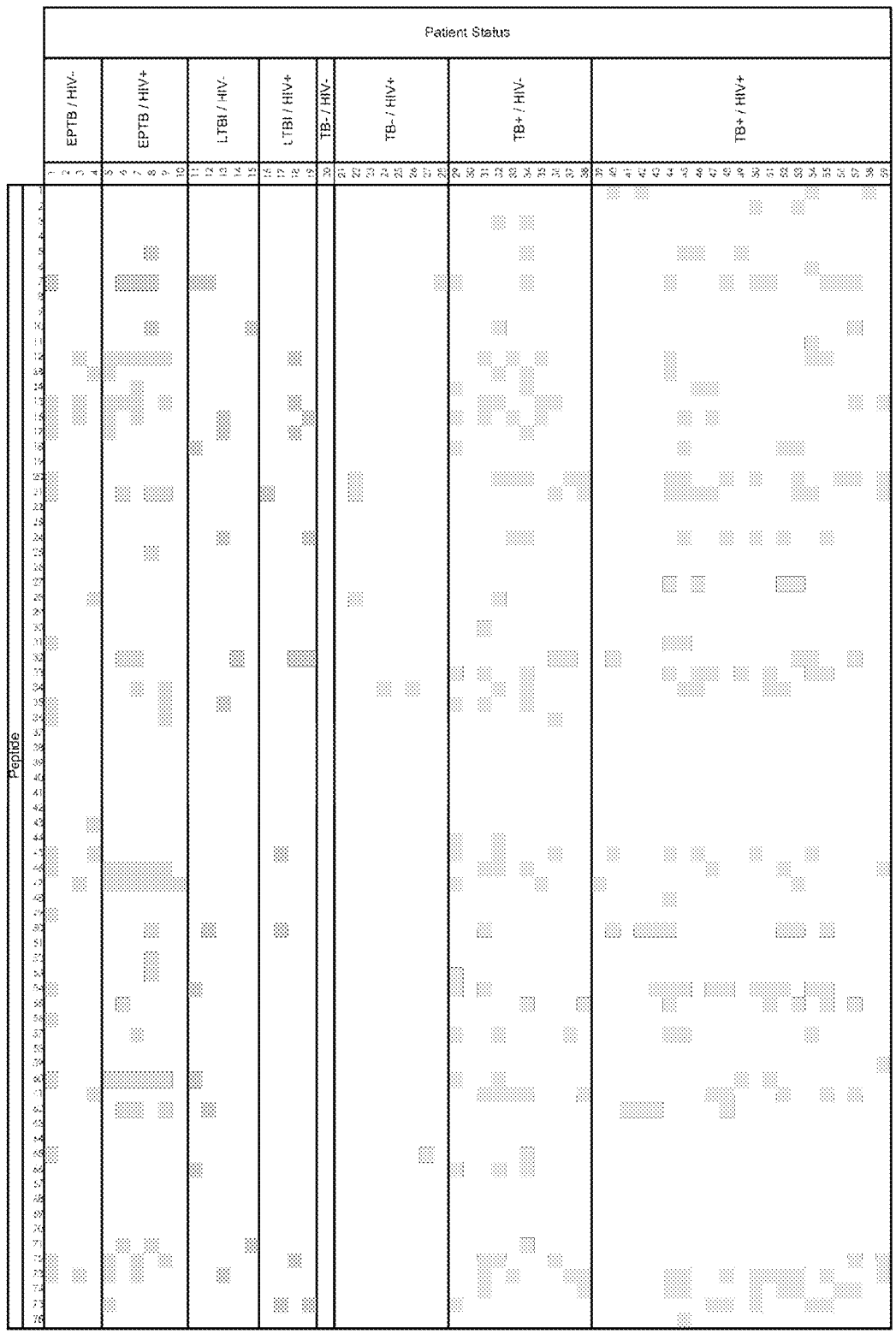
FIG. 10. Heatmap of Peptides Detected by MRM. Colored boxes signify the presence of a peptide above the positive cut-off (the average+2SD for each peptide). The cut-off (or normal reference limit) was determined as the lowest positive value above the highest negative value. Peptides which failed to yield a signal above background are left blank.

A statistical analysis can then be performed to identify which candidate proteins have the highest probability of sensitive detection in a diagnostic assay. FIG. 10 shows an example of an MRM assay used to identify 33 potential Mtb biomarker candidates from a test pool of about 250 potential candidate proteins (also see Example 1).

Proof-of-Concept Tests

After the discovery and validation/qualification stages, the Mtb biomarker candidates can be tested for potential use in a diagnostic assay. Testing of candidate Mtb biomarkers can be achieved through various immunoassays such as, but not limited to Enzyme-linked immunosorbent assay (ELISA). FIG. 8 gives an exemplary list of candidate TB biomarkers that have been processed through a MRM assay as described in Example 1 below. This non-exhaustive list of candidate proteins is a prime target for use in an ELISA proof of concept tests.

It is likely that, since the discovery and validation phases will identify novel TB biomarkers, antibodies will not be available for these proteins and will need to be generated de novo.

The antibodies may be prepared using well-known immunological techniques employing the protein expressed during infection as antigen. Thus, for example, any suitable host (e.g. horse, chicken, murine, rat, sheep or human) may be injected with the protein and the serum collected to yield the desired polyclonal antibody after appropriate purification and/or concentration (for example by affinity chromatography using the immobilized protein as the affinity medium). Alternatively splenocytes or lymphocytes may be recovered from the protein-injected host and immortalized using for example the method of Kohler et al. (1976, *Eur. J. Immunol.*, 6: 511), the resulting cells being segregated to obtain a single genetic line producing monoclonal antibodies. The antibody may be a whole antibody or an antigen binding fragment thereof and may in general belong to any immunoglobulin class. Thus, for example, it may be an immunoglobulin M antibody or an immunoglobulin G antibody. Antibody fragments may be produced using conventional techniques, for example, by enzymatic digestion with pepsin or papain. Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described, for example, in PCT/GB88/0747).

Where it is desired to produce recombinant antibodies according to the invention, these may be produced using, for example, the methods described in EP Specification Nos. 171469, 173494, 194276 and 239400.

Protein Signature

A protein signature can reflect the particular biomarkers that are present on an exosome. In addition, a protein signature can also reflect one or more biomarkers that are carried in an exosome. Alternatively, a protein signature can comprise a combination of one or more biomarkers that are present on an exosome with one or more biomarkers that are detected in the exosome. Moreover, a protein signature can also include fragments or derivatives of proteins.

In a preferred embodiment, the protein signature of an exosome is indicative of an active Mtb infection. FIG. 7 is an exemplary list of Mtb proteins that can function to define a protein signature. These Mtb proteins can include, but are not always limited to, Rv0066c, Rv0125, Rv0129c, Rv0350, Rv0363c, Rv0440, Rv0467, Rv0934, Rv0969, Rv1091, Rv1270c, Rv1469, Rv1827, Rv1837c, Rv1860, Rv1886c, Rv1908c, Rv1926c, Rv1980c, Rv2031c, Rv2220, Rv2244, Rv2376c, Rv3388, Rv3418c, Rv3803c, Rv3804c, Rv3841, Rv3874, and Rv3875. A protein signature can be at least one of these proteins, but can also be 2, 3, 4, 5, 6, 7, 8, 9, 10, 11, 12, 13 . . . etc. For example, some embodiments can contain Ag85a (Rv3804c), Ag85b (Rv1886c), Ag85c (Rv0128c), PepA (Rv0125), PstS1 (Rv0934), CtpD (Rv1469), GlcB (Rv1837c), Apa/Mpt32 (Rv1860), Mpt64 (Rv1980c), HspX (Rv2031), GlnA1 (Rv2220), Fba (Rv0363c), MrsA (Rv3441c), and Hrp1 (Rv2626c) or fragments or derivatives thereof. In another embodiment, a protein signature diagnostic of an active Mtb infection can contain DnaK (Rv0350), PstS1 (Rv0934), AcpM (Rv2244), GlcB (Rv1837) and HspX (Rv2031) or fragments or derivatives thereof. In yet another embodiment, for example, the protein signature can contain DnaK (Rv0350), PstS1 (Rv0934) and HspX (Rv2031) or fragments or derivatives thereof. In still another embodiment, the protein signature can contain DnaK (Rv0350), PstS1 (Rv0934), AcpM (Rv2244), GlcB (Rv1837) and HspX (Rv2031) or fragments thereof. In another embodiment, the protein signature can contain KatG (Rv1908c), Antigen 85a (Rv3804c), Antigen 85b (Rv1886c), and Antigen 85c (Rv0129c) or fragments or derivatives thereof.

In still further embodiments, the protein signature can comprise fragments or derivatives of Mtb biomarker protein. Table 1 below is an exemplary list of peptides and their parent Mtb biomarker proteins that that may be found in or on Mtb infected exosomes (also see FIG. 8).

TABLE 1

| Gene/Protein Name | Peptide Sequence(z) |
|---|---|
| Rv0009/PpiA | IALFGNHAPK(3) (SEQ ID NO: 14)<br>VIQGFMIQGGDPTGTGR(2) (SEQ ID NO: 15) |
| Rv0066c/Icd2 | GISNFHSPSDVIVDASMPAMIR(3) (SEQ ID NO: 16)<br>LPNISASVPQLVAAIK(2) (SEQ ID NO: 17) |
| Rv0125/PepA | TQDVAVLQLR(2) (SEQ ID NO: 18)<br>TQDVAVLQLR(2) (SEQ ID NO: 19) |
| Rv0129c/Ag85c | FLEGLTLR(2) (SEQ ID NO: 20)<br>VQFQGGGPHAVYLLDGLR(3) (SEQ ID NO: 21) |
| Rv0350/DnaK | TTPSIVAFAR(2) (SEQ ID NO: 22)<br>ITQDLLDR(2) (SEQ ID NO: 23) |
| Rv0363c/Fba | LYTSPEDFEK(2) (SEQ ID NO: 24)<br>SEIEEALR(2) (SEQ ID NO: 25)<br>LRPDILAQGQQVAAAK(3) (SEQ ID NO: 26) |
| Rv0440/GroEL2 | AAVEEGIVAGGGVTLLQAAPTLDELK(2) (SEQ ID NO: 27) |
| Rv0934c/PstS1 | ASFLDQVHFQPLPPAVVK(3) (SEQ ID NO: 28)<br>GLGEAQLGNSSGNFLLPDAQSIQAAAAGFASK(3) (SEQ ID NO: 29)<br>SDGSGDTFLFTQYLSK(2) (SEQ ID NO: 30) |
| Rv1270c/LprA | ITGNSSADDIATLAGSR(2) (SEQ ID NO: 31) |
| Rv1469/CtpD | VVAASELVVGDR(2) (SEQ ID NO: 32) |
| Rv1827/GarA | LVFLTGPK(2) (SEQ ID NO: 33)<br>HPDSDIFLDDVTVSR(3) (SEQ ID NO: 34) |
| Rv1837c/GlcB | ATIEQLLTIPLAK(2) (SEQ ID NO: 35)<br>NYTAPGGGQFTLPGR(2) (SEQ ID NO: 36) |
| Rv1837c/GlcB | VVFINTGFLDR(2) (SEQ ID NO: 37)<br>FALNAANAR(2) (SEQ ID NO: 38) |
| Rv1860/Apa | TTGDPPFPGQPPPVANDTR(2) (SEQ ID NO: 39) |
| Rv1886c/Ag85b | PGLPVEYLQVPSPSMGR(3) (SEQ ID NO: 40)<br>WETFLTSELPQWLSANR(2) (SEQ ID NO: 41)<br>NDPTQQIPK(2) (SEQ ID NO: 42) |
| Rv1908c/KatG | EATWLGDER(2) (SEQ ID NO: 43)<br>FAPLNSWPDNASLDK(2) (SEQ ID NO: 44)<br>TFGFGFGR(2) (SEQ ID NO: 45) |
| Rv1926c/Mpt63 | GSVTPAVSQFNAR(2) (SEQ ID NO: 46)<br>TADGINYR(2) (SEQ ID NO: 47) |
| Rv1932/Tpx | DSFGEDYGVTIADGPMAGLLAR(2) (SEQ ID NO: 48) |

TABLE 1-continued

| Gene/Protein Name | Peptide Sequence(z) |
|---|---|
| Rv1980c/Mpt64 | GTQAVVLK(2) (SEQ ID NO: 49)<br>VYQNAGGTHPTTTYK(3) (SEQ ID NO: 50)<br>FLSAATSSTPR(2) (SEQ ID NO: 51)<br>AFDWDQAYR(2) (SEQ ID NO: 52)<br>SLENYIAQTR(2) (SEQ ID NO: 53)<br>EAPYELNITSATYQSAIPPR(2) (SEQ ID NO: 54) |
| Rv2031c/HspX | AELPGVDPDK(2) (SEQ ID NO: 55)<br>DGQLTIK(2) (SEQ ID NO: 56)<br>TVSLPVGADEDDIK(2) (SEQ ID NO: 57) |
| Rv2220/GlnA1 | GGYFPVAPNDQYVDLR(2) (SEQ ID NO: 58)<br>IPITGSNPK(2) (SEQ ID NO: 59) |
| Rv2220/GlnA1 | LVPGYEAPINLVYSQR(2) (SEQ ID NO: 60)<br>SVFDDGLAFDGSSIR(2) (SEQ ID NO: 61) |
| Rv2244/AcpM | IESENPDAVANVQAR(2) (SEQ ID NO: 62)<br>LEEENPEAAQALR(2) (SEQ ID NO: 63)<br>IPDEDLAGLR(2) (SEQ ID NO: 64)<br>TVGDVVAYIQK(2) (SEQ ID NO: 65) |
| Rv2376c/Cfp2 | GSLVEGGIGGTEAR(2) (SEQ ID NO: 66)<br>SLADPNVSFANK(2) (SEQ ID NO: 67) |
| Rv2626c/Hrp1 | DSIYYVDANASIQEMLNVMEEHQVR(3) (SEQ ID NO: 68)<br>GLAAGLDPNTATAGELAR(3) (SEQ ID NO: 69) |
| Rv2780/Ald | GLSTHEGALLSER(3) (SEQ ID NO: 70) |
| RV2878c/Mpt53 | LQFTATTLSGAPFDGASLQGK(2) (SEQ ID NO: 71) |
| Rv3248c/SahH | EYAEVQPLK(2) (SEQ ID NO: 72)<br>GVTEETTTGVLR(2) (SEQ ID NO: 73) |
| Rv3418c/GroES | DVLAVVSK(2) (SEQ ID NO: 74)<br>ILVQANEAETTTASGLVIPDTAK(3) (SEQ ID NO: 75)<br>RIPLDVAEGDTVIYSK(3) (SEQ ID NO: 76) |
| Rv3441c/MrsA | LAATVADAVSTAR(2) (SEQ ID NO: 77)<br>VIAINAEPNGR(2) (SEQ ID NO: 78)<br>YVLEELR(2) (SEQ ID NO: 79) |
| Rv3803c/FbpD | WHDPWVHASLLAQNNTR(3) (SEQ ID NO: 80) |
| Rv3804c/Ag85a | FLEGFVR(2) (SEQ ID NO: 81)<br>NDPLLNVGK(2) (SEQ ID NO: 82) |
| Rv3804c/Ag85a | ALGATPNTGPAPQGA(2) (SEQ ID NO: 83)<br>VQFQSGGANSPALYLLDGLR(3) (SEQ ID NO: 84) |
| Rv3841/BfrB | AGANLFELENFVAR(2) (SEQ ID NO: 85)<br>TVTDQVGR(2) (SEQ ID NO: 86)<br>EALALALDQER(2) (SEQ ID NO: 87) |
| Rv3874/Cfp10 | GAAGTAAQAAVVR(2) (SEQ ID NO: 88)<br>QELDEISTNIR(2) (SEQ ID NO: 89)<br>TQIDQVESTAGSLQGQWR(3) (SEQ ID NO: 90) |
| Rv3875/ESAT-6 | WDATATELNNALQNLAR(2) (SEQ ID NO: 91) |

Furthermore, in some embodiments, the protein signature contains proteins not yet discovered by the method disclosed herein. Moreover, these yet unknown proteins can be a protein signature in and of themselves, or in conjunction with another undiscovered Mtb biomarker protein. Further, these undiscovered proteins can form a protein signature in conjunction with already known Mtb biomarkers, such as the ones describes above.

In another embodiment, a protein signature consists of Mtb biomarker proteins and exosomal markers such as, but not limited to MHC Class I protein, LAMP1, CD9, CD63 and CD81. Other biomarkers found in or on the exosome can also be part of a protein signature.

In a further embodiment, the protein signature can also be diagnostic of a TB disease state and disease progression. FIG. 3 shows an analysis of Mtb proteins identified in exosomes from Mtb infected mice over a 112 day infection period. Using such data, a protein signature can be made to determine which stages of infection a person is in. For example, the presence or absence of certain proteins can be associated with an early stage of disease. Likewise, the presence or absence of other proteins may be a protein signature of a late infection. Also see FIG. 8 and FIG. 11, as well as Example 1 for examples of a protein signature indicative of pulmonary TB, Extrapulmonary TB, and TB– (including latent TB).

In addition, the protein signature may also include proteins and peptides sharing a sequence identity or substantial sequence identity to those proteins and peptides listed herein.

As used herein, "sequence identity" or "identity" in the context of two protein or peptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The term "substantial identity" in the context of a proteins or peptide indicates that a proteins or peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, J M B, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, the invention also provides nucleic acid molecules and peptides that are substantially identical to the nucleic acid molecules and peptides presented herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Diagnostic Tests to Identify Individuals with Active TB Infections

Ideally, several methods, including ELISA, Dipstick tests, lateral flow, microfluidic devices, and microarrays can be used to detect exosomal TB biomarkers in patients with active TB infections.

ELISA, as described above, is a widely used method for the detection of specific proteins in a biological sample. It involves the immobilization of an antibody (primary antibody) to a solid support such as plastic microplates, and detecting a specific antigen via binding to the immobilized antibody, followed by addition of secondary antibody or antibodies, the latter usually being conjugated to enzymes such as alkaline phosphatase or horseradish peroxidase in order to facilitate detection. Addition of a chemical substrate of the enzyme results in the development of a colored reaction product, which indicates the presence of the antigen of interest in the sample.

Hence, according to a preferred embodiment, the immune affinity procedure may be an ELISA immunoassay selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

In one embodiment, detection is effected through capture ELISA. Capture ELISA (also known as "sandwich" ELISA) is a sensitive assay to quantify picogram to microgram quantities of substances (such as hormones, cell signaling chemicals, infectious disease antigens and cytokines.). This type of ELISA is particularly sought after when the substance to be analyzed may be too dilute to bind to the microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. Optimally, the appropriate negative and positive controls should also be included.

The capture or coating antibody to be used should be diluted in carbonate-bicarbonate buffer or PBS. Capture antibodies are typically plated at 0.2 to 10 µg/mL. It is preferable to use affinity purified antibodies or at a minimum use an IgG fraction. Generally samples are diluted in PBS in the 10 ng-10 µg (per mL) range (the more sensitive the assay, the less sample is required).

Detection of the biomarkers or of any fragment or derivative thereof, may be performed using antibodies specific to said biomarkers. These antibodies may be labeled directly or indirectly by a detectable moiety.

As used herein in the specification, the term "detectable moiety" refers to any atom, molecule or a portion thereof, the presence, absence or level of which may be monitored directly or indirectly. One example includes radioactive isotopes. Other examples include (i) enzymes which can catalyze color or light emitting (luminescence) reactions and (ii)

fluorophores. The detection of the detectable moiety can be direct provided that the detectable moiety is itself detectable (i.e. can be directly visualized or measured), such as, for example, in the case of fluorophores. Alternatively, the detection of the detectable moiety can be indirect. In the latter case, a second moiety that reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the anti-biomarker antibody in the method of the invention. This secondary antibody may be itself conjugated to a detectable moiety. One of the ways in which an antibody in accordance with the present invention can be detectably labeled is by linking the same to an enzyme. The enzyme, in turn, when exposed to an appropriate substrate, will react with the substrate in such a manner as to allow its detection, for example by producing a chemical moiety which can be detected, for example, by spectrophotometric, fluorometric or by visual means. Enzymes which can be used to label the antibody include, but are not limited to, horseradish peroxidase, alkaline phosphatase, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase, or any other enzyme which can be conjugated to an antibody and its reaction with a substrate, measured (or detected).

The detection can be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include, but are not limited to, are large beads, e.g., of polystyrene, filter paper, slides, chips, test tubes, and microtiter plates. The first antibody may be bound to the solid support by covalent bonds or by adsorption. The advantage of the use of a solid support is that no centrifugation step is needed for the separation of solid and liquid phase.

The solid support mentioned above can include polymers, such as polystyrene, agarose, Sepharose, cellulose, glass beads and magnetizable particles of cellulose or other polymers. The solid-support can be in the form of large or small beads or particles, tubes, plates, slides, chips or other forms.

As a solid support, use is preferably made of a test tube, or a microtiter plate the inner walls of which are coated with a first antibody, e.g., antibodies specific to a peptide or protein from Table 1 and FIG. 7, or of any fragment or derivative thereof.

In a further embodiment, Dipstick assays can used to detect exosomal Mtb biomarkers. Dipstick assays use the well-established lateral flow format, wherein capture antibodies are striped or banded onto nitrocellulose membrane and a wicking pad draws the sample up through the dipstick, whereby the exosomal Mtb biomarkers interact with an Mtb biomarker antibody, or combination of antibodies. Other antibodies specific to exosomal biomarkers, or other proteins of interest can be included. Subsequent analysis of enzyme activity and protein quantity can be done using standard methods known to a person skilled in the art, or as discussed above regarding ELISAs.

In another preferred embodiment, Microfluidic devices, which may also be referred to as "lab-on-a-chip" systems, biomedical micro-electro-mechanical systems (bioMEMs), or multicomponent integrated systems, can be used for detecting exosomal Mtb biomarkers. Such systems miniaturize and compartmentalize processes that allow for detection of exosomal biomarkers, and other processes.

Array-based assays and bead-based assays can be used with microfluidic device. For example, a binding agent can be coupled to beads and the binding reaction between the beads and TB biomarker can be performed in a microfluidic device. Multiplexing, or detecting more than one TB biomarker at once, can also be performed using a microfluidic device. Different compartments can comprise different binding agents for different populations of TB biomarkers, where each population has a different bio-signature.

In another embodiment, microarrays are used to detect exosomal Mtb biomarkers. Microarrays are typically small, high throughput chips generally made of a solid support structure, typically glass slides, nitrocellulose, or microtiter plates. Generally, antibodies to specific biomarker are bound to the solid support; however, other molecules, such as, but not limited to other proteins, aptamers, DNA, RNA, sugars or lipids can be bound to the solid surface as well. Detection of the captured biomarker can be accomplished as discussed above for ELISA detection.

In another further embodiment, recognition of exosomal TB specific biomarker is achieved through an immune affinity procedure is any one of Western Blot, immuno-precipitation, FACS, Biochip array, Lateral Flow, Time Resolved Fluorometry, ECL procedures, or any procedure based on immune recognition known to one of ordinary skill in the art.

A Kit for Diagnosis of Mtb Infection

The present disclosure is also directed to a kit or system useful for practicing the methods described herein. The kit can be a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assays described herein, including, but not limited to a means of detection and a means to detect the recognition of the detection. Alternatively, a kit may only include a detection device having a means for detection of Mtb biomarker proteins or fragments thereof, and a means for recognition of the detection. Alternatively, the kit may only include a detection device having a means of detecting the Mtb biomarker proteins or fragments thereof.

A means of detection may be an antibody specific to an Mtb biomarker, for example an antibody specific to any one of Mtb specific biomarkers described herein, or any fragment or derivative thereof, in particular an antibody specific to Rv0066c, Rv0125, Rv0129c, Rv0350, Rv0363c, Rv0440, Rv0467, Rv0934, Rv0969, Rv1091, Rv1270c, Rv1469, Rv1827, Rv1837c, Rv1860, Rv1886c, Rv1908c, Rv1926c, Rv1980c, Rv2031c, Rv2220, Rv2244, Rv2376c, Rv2626c, Rv3388, Rv3418c, Rv3441c, Rv3803c, Rv3804c, Rv3841 and Rv3874 or a combination thereof. In certain embodiments, the antibody can be an antibody specific to one or more of Rv0009c, Rv0066c, Rv0125, Rv0129c, Rv0350, Rv0363c, Rv0440, Rv0467, Rv0934, Rv1270c, Rv1469, Rv1827, Rv1837c, Rv1860, Rv1886c, Rv1908c, Rv1926c, Rv1932, Rv1980c, Rv2031c, Rv2220, Rv2244, Rv2376c, Rv2626c, Rv2780, Rv2878c, Rv3248c, Rv3388, Rv3418c, Rv3441c, Rv3803c, Rv3804c, Rv3841, Rv3874, and Rv3875, or a combination thereof.

In other embodiments, antibodies can be specific to Mtb biomarkers, or a fragment or derivative thereof, including Ag85a (Rv3804c), Ag85b (Rv1886c), Ag85c (Rv0129c), PepA (Rv0125), PstS1 (Rv0934), CtpD (Rv1469), GlcB (Rv1837c), Apa/Mpt32 (Rv1860), Mpt64 (Rv1980c), HspX (Rv2031c), GlnA1 (Rv2220), Fba (Rv0363c), MrsA (Rv3441c), and Hrp1 (Rv2626c) or a combination thereof (also see FIG. 8 and Table 1 for a list of exemplary peptide fragments). Alternatively, in some embodiments, an aptamer can be used to detect Mtb biomarkers. Alternatively, the means of detection is a substance that recognizes or detects the Mtb biomarkers through their biological activity or structural feature. One example of biological activity is an enzymatic activity, wherein an enzyme substrate would be the recognition agent. In such case, recognition and possibly binding would lead to an observable alteration or change in the catalytic activity of said enzyme or of the enzyme substrate.

The means of detection may therefore be a protein-based, carbohydrate-based, lipid-based, natural organic-based, synthetically derived organic-based, or inorganic-based material, or any small molecule. The means of detection may also be a detection device such as a Dipstick tests, microfluidic devices, microarrays and other lateral flow devices.

In a further embodiment of the kit provided herein, at least one reagent is provided for the detection of the recognition of at least one means of detecting the Mtb specific biomarker is detected by suitable means. Suitable means may be an immune affinity procedure, an enzymatic assay, or means for detecting a structural feature, amongst others.

In another further embodiment, the detection of recognition of at least one means of detecting Mtb biomarker is achieved through an immune affinity procedure is any one of enzyme-linked immunosorbent assay (ELISA), Western Blot, immuno-precipitation, FACS, Biochip array, Lateral Flow, Time Resolved Fluorometry, ECL procedures, or any procedure based on immune recognition.

In some embodiments, the kit may comprise a detection device having at least one compartment. One compartment may have an array of at least one means of detection wherein each means of detection is located in a defined position in the array. The term "array" as used by the methods and kits of the invention refers to an "addressed" spatial arrangement of the recognition means. Each "address" of the array is a predetermined specific spatial region containing a recognition agent. For example, an array may be a plurality of vessels (test tubes), plates, micro-wells in a micro-plate each containing a different antibody. An array may also be any solid support holding in distinct regions (dots, lines, columns) different and known recognition agents, for example antibodies. The array preferably includes built-in appropriate controls, for example, regions without the sample, regions without the antibody, regions without either, namely with solvent and reagents alone and regions containing synthetic or isolated proteins or peptides, corresponding to the biomarkers (positive control). Solid support used for the array of the invention will be described in more detail herein after, in connection with the kits provided by the invention.

A solid support suitable for use in the kits of the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as micro-titer plates or microplates), membranes, filters, conducting and non-conducting metals, glass (including microscope slides) and magnetic supports. More specific examples of useful solid supports include silica gels, polymeric membranes, particles, derivatized plastic films, glass beads, cotton, plastic beads, alumina gels, and polysaccharides such as Sepharose, nylon, latex bead, magnetic bead, paramagnetic bead, superparamagnetic bead, starch and the like. It should be further noted that any of the reagents included in any of the methods and kits of the invention may be provided as reagents embedded, linked, connected, attached placed or fused to any of the solid support materials described above.

An exemplary kit disclosed herein may contain, for example, any combination of:
(a) at least one means of detecting an Mtb biomarker protein or a fragment there of that is indicative of an active Mtb infection;
(b) the at least one protein of fragment thereof selected from the group consisting of Rv0066c, Rv0125, Rv0129c, Rv0350, Rv0363c, Rv0440, Rv0467, Rv0934, Rv0969, Rv1091, Rv1270c, Rv1469, Rv1827, Rv1837c, Rv1860, Rv1886c, Rv1908c, Rv1926c, Rv1980c, Rv2031c, Rv2220, Rv2244, Rv2376c, Rv2626c, Rv3388, Rv3418c, Rv3441c, Rv3803c, Rv3804c, Rv3841 and Rv3874 or a combination thereof;
(c) at least one reagent that allows the detection of antibody-Mtb biomarker interaction;
(d) a means of collecting a sample;
(e) a detection device;
(f) a reaction compartment containing at least one means to detect the Mtb biomarker or fragment thereof;
(g) a control sample
(h) a means of isolating exosomes from the sample;

The sample that is taken can originate from any bodily fluid such as, for example, blood, serum, urine, or saliva. Moreover, the means of detection can also be, in some embodiments, an ELISA or other immunoassay. Further, the means of detecting an Mtb biomarker protein of fragment thereof can be a microfluidic device, lateral flow device or microarray device.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more peptides of a protein refers to one to five, or one to four, for example if the protein is fragmented.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

"Protein" as used herein refers to a biological molecule comprised of a chain of amino acids.

"Peptide" as used herein refers to a short chain of amino acids.

"Antibody" as used herein refers to an immunoglobulin capable of binding an antigen.

"Biomarkers" as used herein refer to a distinct biochemical, genetic, or molecular characteristic or substance that is an indicator of a particular biological condition or process.

"Antigen" as used herein refers to a substance capable of binding to a specific antibody.

"Protein signature" as used herein refers to at least one protein or fragments thereof that when present, is indicative a specific phenotype.

"Fragment" as used herein refers to any subset of a protein that is less than the whole protein.

"Phenotype as used herein refers to any observable characteristic or trait of a subject, such as a disease or condition, or a disease stage or condition stage.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

A Multiplexed Peptide Assay for the Detection of TB Biomarkers in Exosomes

This study concentrates on a simplified fraction of serum, namely exosomes, focusing on the bacterial proteins enriched within these exosomes (exo-proteome). Exosomes are 30-100 nm vesicles constitutively released from most eukaryotic cell types into the lymphatic system and blood to facilitate systemic, as well as local intercellular communication. Exosomes are an ideal source of biomarkers of chronic diseases, especially intracellular infections like TB, since their release appears to be stimulated by inflammation and hypoxia and since their contents are attributed to their cell of origin, reflecting cellular abnormalities and disease state. We recently identified over 250 potential biomarkers, both host and pathogen derived, from Mtb-infected macrophages and biological fluids from Mtb-infected animal models and humans. From these initial studies, we hypothesize that exosomes isolated from serum of patients with active TB would contain specific peptide fingerprints indicative of active TB that would not be found in patients without active TB.

Here, the applicants report the generation of a proteomic workflow for serum exosomes that includes rational development of Multiple-Reaction Monitoring (MRM) assays using novel Mtb biomarkers in order to develop peptide bioassays diagnostic of active TB.

Experimental Procedures

Study Participants. Between July 2007 and July 2009, the applicants prospectively enrolled two groups of patients. The first, a randomly selected case series of patients with confirmed culture-positive pulmonary tuberculosis, and the second, a consecutive random sample of adults (age≥18 years), hereafter called the evaluation sample. All patients in both groups were newly admitted to the medical wards of Mulago Hospital (Kampala, Uganda) with cough≥2 weeks. The applicants excluded patients with concurrent or previous TB treatment in the previous two years. The applicants collected demographic and clinical information from all patients using a standardized questionnaire. All patients underwent chest radiography, collection of blood for HIV antibody testing, CD4+ T-lymphocyte counts, and T-cell interferon gamma release assay testing (T.SPOT.TB, Oxford Immunotec, Oxford, UK), and collection of sputum samples over two consecutive days for AFB smear microscopy and culture, as part of a previously described comprehensive clinical evaluation. Technicians at the Uganda National TB Reference Laboratory performed all mycobacterial studies according to standard protocols. In the latter group of patients, technicians at the Joint Clinical Research Centre performed T-cell assays as previously described, and reported results according to U.S. Food and Drug Administration (FDA) criteria. The applicants invited all patients to return for a follow-up clinical examination and assessment of vital status two months after admission, and for the evaluation sample, made multiple attempts to reach those who failed to return by telephoning them and their close contacts and/or visiting their last known place of residence.

For the second group, the applicants sampled TB cases and non-TB controls nested within the cohort of consecutive patients with chronic unexplained cough, using pre-established reference standard criteria (see online supplement for details). The applicants stratified the TB patients to ensure that the study population included both smear-positive and smear-negative pulmonary disease, as well as extrapulmonary TB (EPTB). The applicants stratified the non-TB patients by the presence or absence of latent TB infection (LTBI). The applicants further stratified both TB and non-TB patients by HIV status. Those performing laboratory assays were initially blinded to all clinical characteristics and disease classification. The Makerere University School of Medicine Research Ethics Committee, the Mulago Hospital Institutional Review Board, the Uganda National Council for Science and Technology, and the UCSF Committee on Human Research approved the clinical protocol, and all patients provided written informed consent for study enrollment and specimen banking.

Exosomes were harvested from blinded human serum via ExoQuick™ (Systems Biosciences, Inc., Mountain View, Calif.) after filtration through a 0.2 micron filter. Protein content of the purified exosomes was quantitated by micro bicinchoninic acid assay (BCA) assay (Thermo Fisher Scientific, Inc. Rockford, Ill.). Twenty .mu.g of protein of each sample was resolved by SDS-PAGE and processed via digestion, as described previously, with modifications. Briefly, samples subjected to full proteomic characterization by LC-MS/MS were divided into ten gel fractions (Giri et al. Proteomics, 2010. 10(17): p. 3190-202) prior to digestion. Exosome samples for MRM-MS were left unfractionated. All samples were digested with trypsin at a 20:1 ratio (sample: protease), as previously published (Giri et al. Proteomics, 2010. 10(17): p. 3190-202).

Mass Spectrometry of Tryptic Peptides. All samples were injected at a concentration of approximately 50-100 ng/mL. Peptides were purified and concentrated using an on-line enrichment column (Agilent Zorbax C18, 5 mm, 560.3 mm column, Agilent 1100 nanoHPLC,). Subsequent chromatographic separation was performed on a reverse phase nanospray column (Zorbax C18, 5 mm, 75 mm ID 6 150 mm column). Samples were eluted into a LTQ linear ion trap (Thermo Scientific) using a flow rate of 300 mL/min with the following gradient profile: 0% B for 0-5 min, 0-15% B for 5-8 min, 15-55% B for 8-98 min, and 55-100% B for 98-103 min (A=3% ACN, 0.1% formic acid; B=100% ACN, 0.1% formic acid). This elongated method has been optimized to separate complex samples, such as whole cell lysate. Mass spectra are collected over an m/z range of 200-2000 Da using a dynamic exclusion limit of 2 MS/MS spectra of a given mass for 30 s (exclusion duration of 90 s). Compound lists of the resulting spectra were generated using Bioworks 3.0 software (Thermo Scientific) with an intensity threshold of 5,000 and 1 scan/group.

Database Searching. All MS/MS samples were analyzed using X! Tandem (The GPM, thegpm.org; version 2007.01.01.1). Mascot (Matrix Science, London, UK; version Mascot) and Sequest (Thermo Fisher Scientific, San Jose, Calif., USA; version v.27, rev. 11). Mascot, Sequest, and X!Tandem was set up to search the TBv3_human_rev_111510 database (111510, 186822 entries) assuming digestion with trypsin with a maximum of 2 missed cleavages; the searches were performed with a fragment ion mass tolerance of 1.00 Da and a parent ion tolerance of 1.5 Da. Oxidation of methionine (+16) and iodoacetamide derivative of cysteine (+57) were specified as variable modifications.

Criteria for Protein Identification. Scaffold (version Scaffold 4.1.1, Proteome Software Inc., Portland, Oreg.) was used to validate MS/MS based peptide and protein identifications. Peptide identifications were accepted if they could be established at greater than 90.0% probability by the Peptide Prophet algorithm (Keller, A., et al., Anal Chem, 2002. 74(20): p. 5383-92).]. Protein identifications were accepted if they could be established at greater than 90.0% probability and contained at least 1 identified peptide. All proteins identified were subject to manual validation. Protein probabilities were assigned by the Protein Prophet algorithm (Nesvizhskii, A. I., et al., Anal Chem, 2003. 75(17): p. 4646-58.). Proteins that contained similar peptides and could not be differentiated based on MS/MS analysis alone were grouped to satisfy the principles of parsimony.

Peptide Selection and Multiple Reaction Monitoring (MRM) Development. The applicants used Skyline (64-bit) version 1.4.0.4421) to build and optimize the selected reaction monitoring (SRM) methods for the relative and absolute quantification of peptides (MacLean, B., et al., Bioinformatics, 2010. 26(7): p. 966-8). FASTA-formatted sequences of all 36 proteins were used for in silico tryptic (KRIP) digestion and restricting the prediction of peptides to those ranging from 6 to 25 amino acids in length and assuming 100% digestion efficiency. Peptides that included cysteine and methionine were avoided when possible. The initial transitions selected for each peptide included both double and triple charged precursor ions, as well as, monitoring of both b and y ions. The applicants exported the resultant methods to Masslynx (Waters Corporation, Milford, Mass.). Additional methods were developed on peptides identified in previous LC-MS/MS data sets. Skyline was used to predict and optimize collision energies for each peptide (Maclean, B., et al., Anal Chem, 2010. 82(24): p. 10116-24). The final methods included the selection of three transitions per peptide. The applicants performed all method development initially on Mtb culture filtrate proteins (CFP), Mtb whole cell lysate (WCL) or recombinant protein if available (obtained by BEI Resources, NIH, NIAID, http://www.beiresources.org/). Final MRM methods were multiplexed and included monitoring a total of 76 peptides by selecting for unique retention or dwell times ≥0.066 s whenever possible.

Preparation of Matrix Controls for MRM Method Evaluation. The applicants used exosomes isolated from the broncheoalveolar lavage (BAL) fluid, serum and urine from several paired guinea pigs (GP), composed of both uninfected control and Mtb-infected animals. Mtb-infected GPs were used as a positive control to confirm the presence of these peptides within one or multiple fluids. GPs were infected as previously published with modifications. Briefly, GPs were infected with Mtb H37Rv by the low dose aerosol (LDA) method (approximately $10^6$ colony forming units, CFU) with a Madison Chamber (Kruh, N. A., et al., PLoS One, 2010. 5(11): p. e13938; Izzo, A., et al., Tuberculosis (Edinb), 2005. 85(1-2): p. 25-8). In addition, a small aliquot of the suspension was plated on 7H11 media to confirm dose of aerosolized bacilli used in each infection. Samples of urine and blood were collected after sedation with isoflurane, followed by catching spontaneously released urine into sterile, 5 ml polycarbonate snap-cap tubes and aseptic puncture of the subclavian vein. Blood was centrifuged at 10,000×g to remove cells and platelets and recover serum. Samples of BAL fluid were collected by instillation of ice-cold 2% heparin in phosphate-buffered saline (pH 7.4) into the lungs of euthanized guinea pigs (Sjogren, M., et al., Clin Chem, 2001. 47(10): p. 1776-81). All samples were filtered through a 0.2 m filter prior to further use. All animals were handled in strict accordance with good animal practice as defined by the relevant national and/or local animal welfare bodies, and all animal work was approved by the Colorado State University Institutional Animal Care and Use Committee (IACUC #10-2306A). To test for matrix effects, the applicants isolated exosomes from the serum of uninfected GPs to determine the detection limits of select peptides across a range of concentrations of spiked trypsin-digested CFP or WCL. Poor peak intensity, low quality peak resolution, or inability to identify three transition ions in the control samples substantially reduced the number of peptides detected.

Multiple Reaction Monitoring Mass Spectrometry. The applicants performed all CFP analyses using a LC MS/MS system consisting of a Waters nanoACQUITY UPLC coupled to a Waters TQ-S mass spectrometer fitted with a Trizaic source. The instrument was operated in positive electrospray ionization mode using MassLynx V4.1 SCN810 (Waters Corporation, Milford, Mass.). Chromatography was performed on an 85 μm×100 mm Trizaic nanotile packed with BEH C18 1.8 μm. Peptides were separated using gradient elution with a stable flow of 0.50 μL/min Two gradients were utilized: Method 1 (24 minute run time) started with 76% buffer A (99.9% water with 0.1% formic acid (FA)) and 24% buffer B (99.9% acetonitrile (ACN) with 0.1% FA) for 3 minutes, followed by a 10 minute linear gradient to 32% B. From 13 minutes to 16 minutes, buffer B was increased linearly to 85% and put on hold for 2 minutes. At 18.5 minutes the column was allowed to re-equilibrate at 12% B for 6 minutes. Method 2 (15 minute run time) had an initial condition at 14% B, with a linear gradient of 7 minutes of 55% B. At 7.5 minutes, the column was flushed with 85% B for 2 minutes and then re-equilibrated down to 3% B for 5 minutes. The column was maintained at 46° C. during analysis, and the samples were kept at 4° C. The MS was operating in selective reaction mode using electrospray ionization in positive ion mode, with a capillary voltage of 3.4 kV and a source temperature of 100° C. Cone voltage was static at 35 V and the collision energies were optimized for each compound individually. Peak identification and optimization was performed using either MassLynx software version 4.1 or Skyline.

Spectral Analysis. All spectral data was manually inspected in Skyline to confirm that auto-selected peak boundaries provided accurate integration and quantification. The total peak areas for each peptide were calculated by adding the peak areas from all three transition ions and were used to determine the normal reference limit.

Statistical Analysis. The applicants exported total peak areas into Excel and performed principal component analysis (PCA) using SIMCA P+(v.12.0.0.0—www.umetrics.com) to predict peptides that influenced separation between patients with TB (TB+), including both pulmonary TB (PTB) and EPTB versus non-TB patients (TB−), including those with LTBI. Further PCA was performed to determine the contribution, if any, of peptides to distinguish EPTB from PTB. The PCA results were evaluated using unpaired, two-tailed t-tests (Graphpad Prism) to determine if the discriminatory peptides were statistically significant.

Results

Biomarker Candidate Discovery—Rationale

In designing the MRM assays we set out to confirm candidate protein biomarkers identified in three previous studies, including a screening of exosomes isolated from Mtb-infected macrophages, mice and humans. Specifically, 25 proteins were included from our pilot discovery dataset in which bacterial proteins were identified by LC-MS/MS in exosomes isolated from Mtb-infected J774a.1 murine macrophage cells (FIG. 7). Subsequent experiments evaluating the content of exosomes isolated from the BAL fluid from Mtb-infected BALB/c mice, revealed numerous additional potential protein candidates confirming that BAL fluid, derived from the site of the infection, was a rich source of mycobacterial proteins. This dataset included the 25 proteins originally identified from our macrophage results, as well as generated dozens of additional candidates, 5 of which were included in this study (FIG. 7). Lastly, the exo-proteome of sera-derived exosomes from the case series of eight Ugandans diagnosed with active pulmonary tuberculosis was mined for additional candidate biomarkers by LC tandem MS. While only 2 additional proteins were included from this endeavor, the potential relevance of these proteins drives their inclusion in our MRM assays. Of equal importance, this effort also served to confirm several of the proteins previously identified (FIG. 7) and included in the development of our MRM assays.

Adaptation of Shotgun Proteomics to Targeted Analysis

Figure 9:
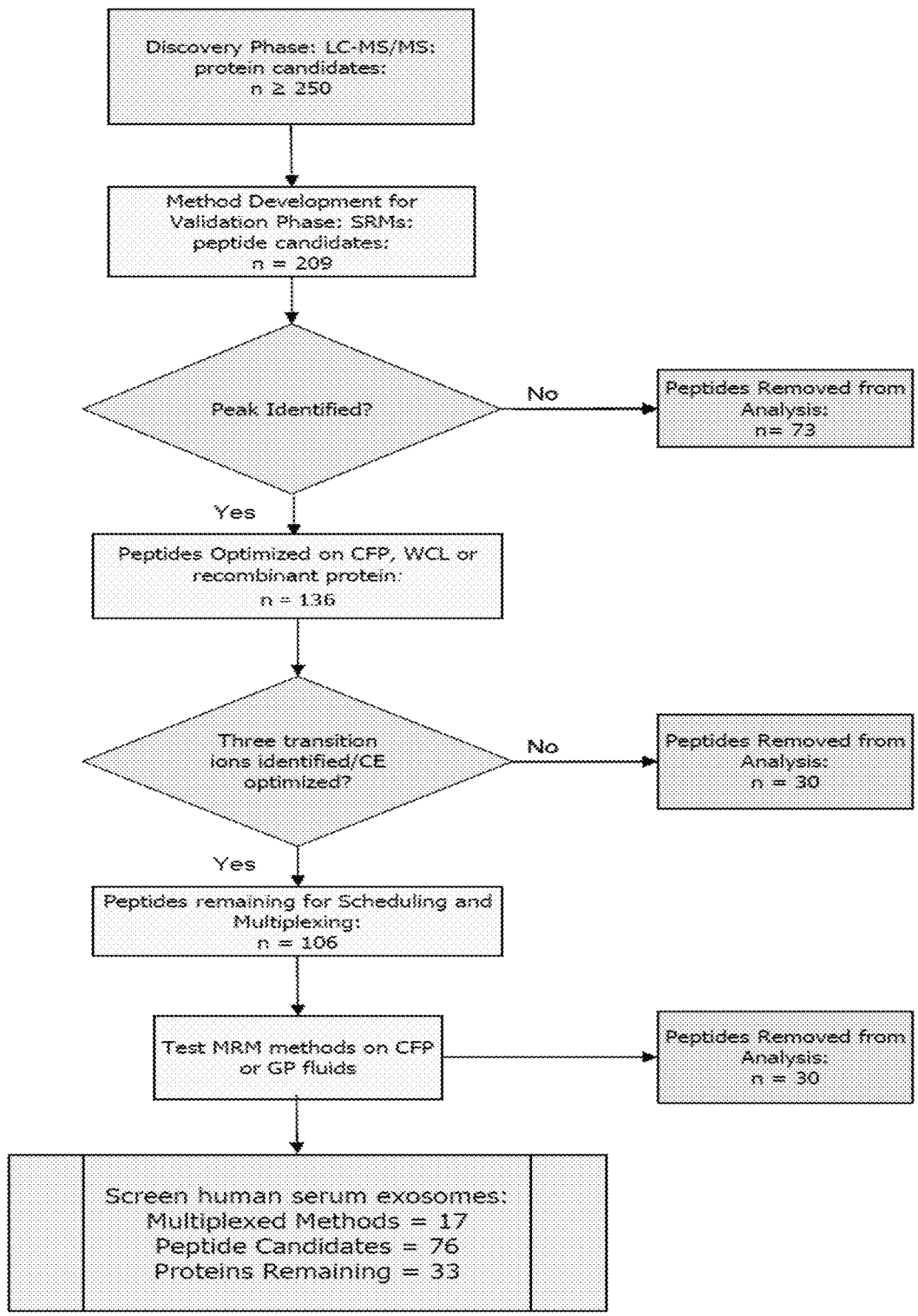
FIG. 9. An example of a decision tree outlining the rationale progression from the discovery phase of Mtb biomarkers using LC-MS/MS through the development of targeted MS assays for the validation of biomarkers in human biological fluids.

Overall, from these discovery phase analyses, over 250 proteins were identified as potential biomarker candidates (FIG. 9). From this initial list, thirty-three of these proteins were chosen for further investigation based on the quality and/or frequency of the spectra observed during MS analysis of biological fluids. Two hundred and nine peptides from these thirty-three proteins underwent SRM development (FIG. 9), whereby LC-MS/MS spectra were interrogated for the most intense transition ions. When data was not available for multiple peptides from each protein, in silico analysis was performed to predict which peptides and transition ions would be most suitable for successful SRM development. The remaining 106 peptides were multiplexed into twenty-four 45-minute methods (FIG. 9), which were further evaluated utilizing exosomes isolated from biofluids collected from the guinea pig model system of tuberculosis infection as a relevant matrix (see Methods). All MRM methods were screened and several peptides were removed due to peak interference with exosome background (FIG. 9). Ultimately, 76 peptides from 33 proteins remained for multiplexing (Table 1) into three 15-minute and fourteen 24-minute, scheduled MRM assays (17 injections over ~7 hours; FIG. 9).

Interrogation of Clinical Samples

The finalized multiplex MRM assays were applied to a small sample set (n=59) of exosomes isolated from serum from Ugandan patients enrolled in the TB evaluation sample. Subjects included those diagnosed with either smear-positive or smear-negative TB (TB+) (n=41), or as not having active TB (TB−) (n=18). The TB+ patients were further subcategorized as having either pulmonary (n=31) or extrapulmonary disease (n=10). The TB− control patients could be categorized as either having no evidence of exposure to Mtb (n=9) or as having latent TB infection (LTBI) (n=9). In general, patients were young, with a high prevalence of advanced, untreated HIV (Table 2 below).

for each peptide; everything above the normal level was considered positive and everything below negative. The results of this decision tree are summarized as a heat map (FIG. 10).

TABLE 2

Demographic and baseline clinical characteristics of Ugandan patients undergoing TB evaluation

| Characteristics N (%) | EPTB (n = 10) | PTB (n = 31) | LTBI (n = 9) | Not TB (n = 9) |
|---|---|---|---|---|
| Female sex | 4 (40) | 19 (61) | 4 (44) | 3 (33) |
| Median age (IQR), years | 34 (26-41) | 29 (23-35) | 31 (25-40) | 35 (21-35) |
| HIV-positive | 6 (60) | 21 (68) | 4 (44) | 8 (89) |
| Median CD4+ count (IQR), cells/μL | 18 (9-39) | 252 (113-337) | 32 (17-392) | 190 (71-240) |
| Antiretroviral therapy* | 3 (14) | 0 (0) | 3 (75) | 0 (0) |
| CTX prophylaxis† | 19 (90) | 6 (100) | 4 (100) | 7 (88) |
| Antibiotics for current illness | 5 (50) | 24 (77) | 4 (44) | 6 (67) |
| Dyspnea | 8 (80) | 19 (61) | 5 (56) | 5 (56) |
| Fever, chills, night sweats | 10 (100) | 31 (100) | 9 (100) | 9 (100) |
| Weight loss (>5 kg)‡ | 10 (100) | 20 (65) | 6 (67) | 3 (33) |
| Cough in past 7 days | 8 (80) | 30 (97) | 7 (78) | 8 (89) |
| Smear-positive | 1 (10) | 24 (77) | 0 (0) | 0 (0) |
| Mycobacterial culture-positive | 3 (30) | 31 (100) | 0 (0) | 0 (0) |

Abbreviations:
IQR, Interquartile range;
N, number;
PTB, Pulmonary tuberculosis;
EPTB, Extra-pulmonary tuberculosis;
LTBI, Latent tuberculosis infection;
TB, Tuberculosis;
HIV, Human immunodeficiency virus;
CTX, Co-trimoxazole prophylaxis;
kg, kilograms.
Legend:
*14 missing values (9 PTB, 1 LTBI, 4 Not TB),
†1 missing value (PTB),
‡7 missing values (5 PTB, 1 LTBI, 1 Not TB).

Raw data from the MRM assays were processed into total peak area for each monitored peptide. From this data, we calculated the normal reference limit for each peptide by determining the maximum peak area in the TB− specimens. Values with total peak area intensities above this level were scored as a positive signal. Many of the peptides were not detected above the normal reference level in any patient sample (n=22), and thus were not considered in our follow up analyses. The proportion of TB+ patients exceeding the normal reference limit ranged between 0-41% for a given peptide. All but one patient with active TB (PTB and EPTB) contained at least one peptide marker (98%), with an average of ~8 peptides detected per patient and ranging from 0 to 18 peptides identified. The proportion of TB patients with a positive MRM assay did not vary by smear status; no significant differences were seen between the number or identity of the peptides found in smear-negative (average of 7.43 peptides) TB samples when compared to the smear-positive (7.46 peptides) TB samples. Similarly, HIV status did not affect the number of peptides observed among TB samples, with an average of 7.63 and 8.14 peptides observed in HIV+ versus HIV− patients. All LTBI samples had a positive signal for at least one Mtb peptide. On average, 3 Mtb peptides were detected per LTBI sample, with a range from one to five peptides identified. There was a 1% false positive rate in our TB− samples, excluding the LTBI group; which increases to 2.6% when LTBI is included.

Preliminary Fingerprint of Active TB

The initial workflow utilized boxplots to summarize the MRM data for each peptide, detailing the total peak areas comparing the TB+ and TB− samples. Normal reference limits were generated from boxplots affording binary decisions for each peptide; everything above the normal level was considered positive and everything below negative. The results of this decision tree are summarized as a heat map (FIG. 10). Candidate peptides with binary scores under 4 (equating to presence in under 10% of all TB+ samples) disqualified an additional 24 peptides from further consideration as biomarker candidates; leaving 30 peptides for future screening and validation.

Stratification of TB Status by Biomarker

Figure 11A:
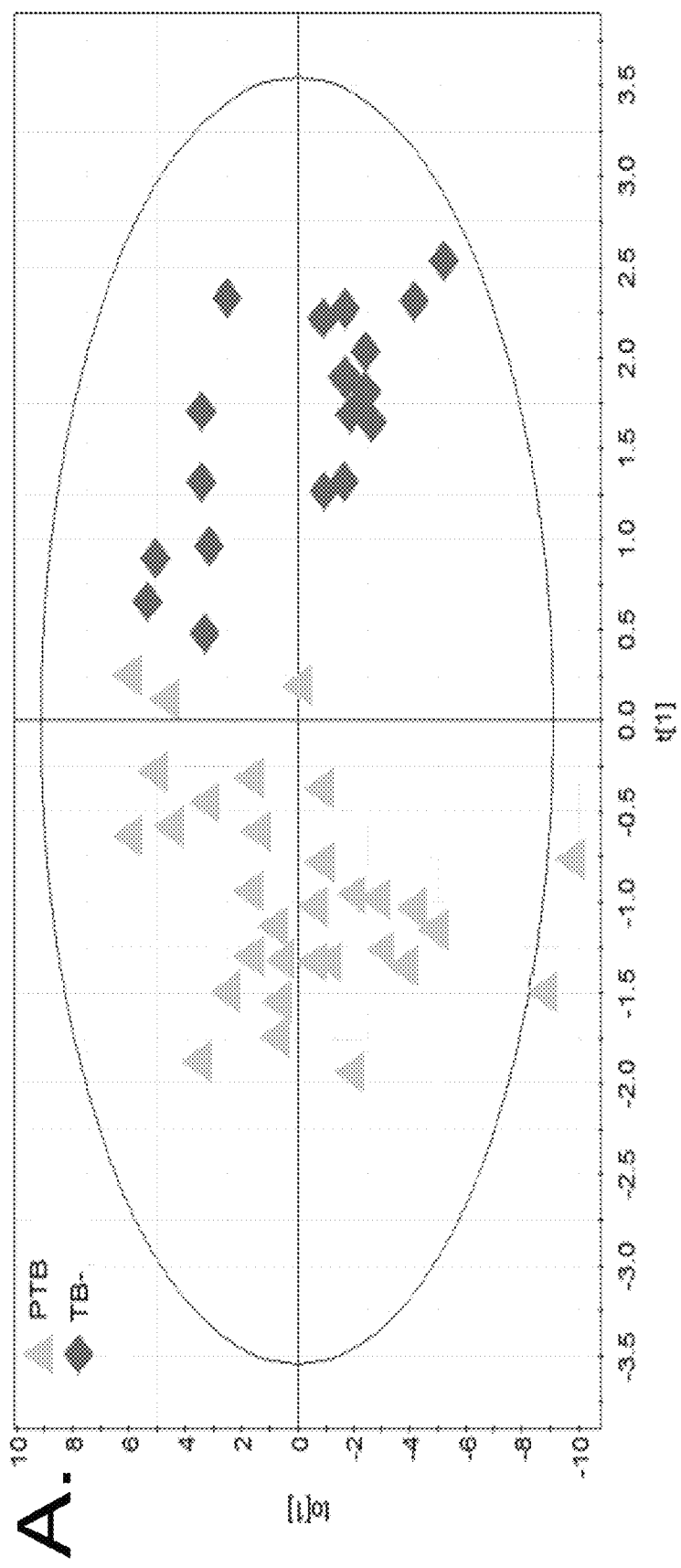
FIG. 11. (A) Separation between PTB+ (blue) and TB− (pink) samples. (B) Separation between EPTB+ (green) and TB− (pink) samples. (C) OPLS Plot Separates Pulmonary TB (blue triangles) from EPTB (green diamonds). These plots include all peptide data scaled by UV.
Figure 11B:
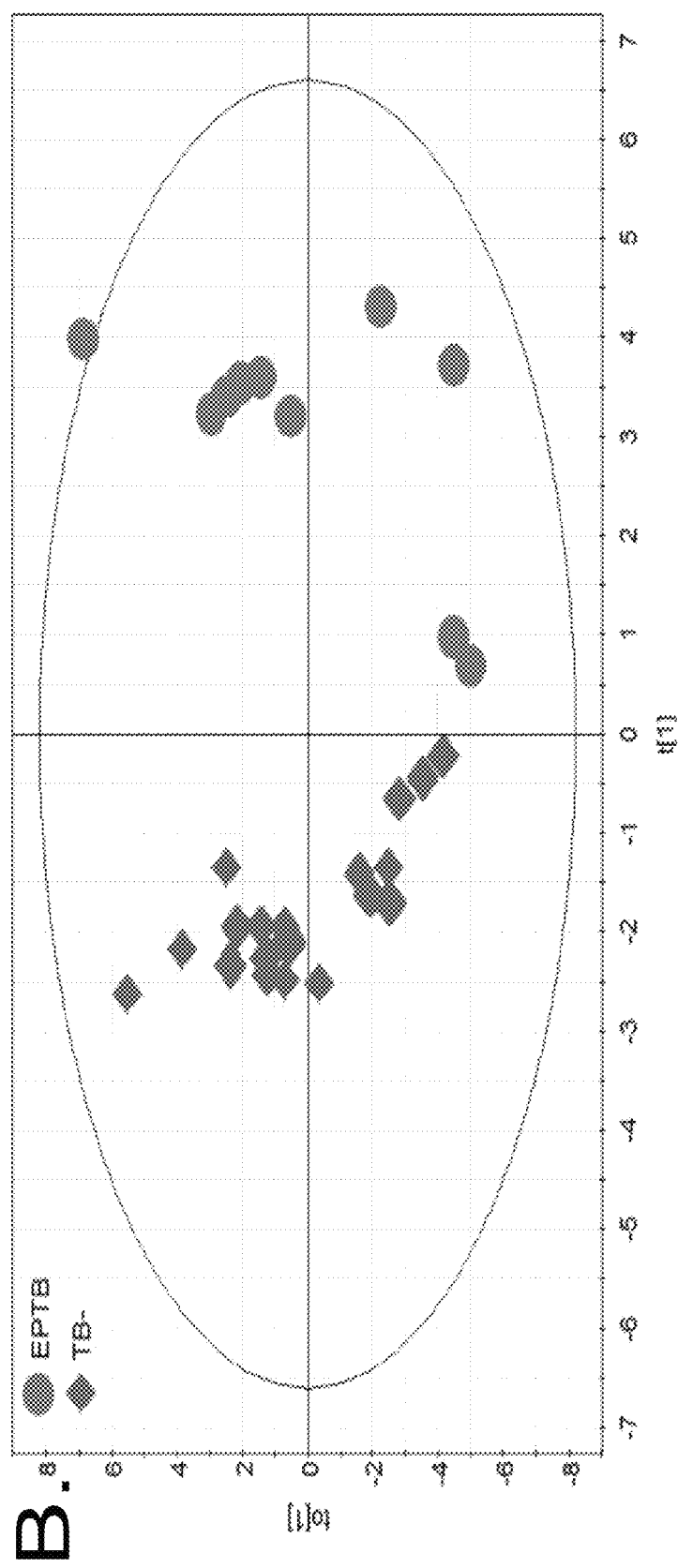
Figure 11C:
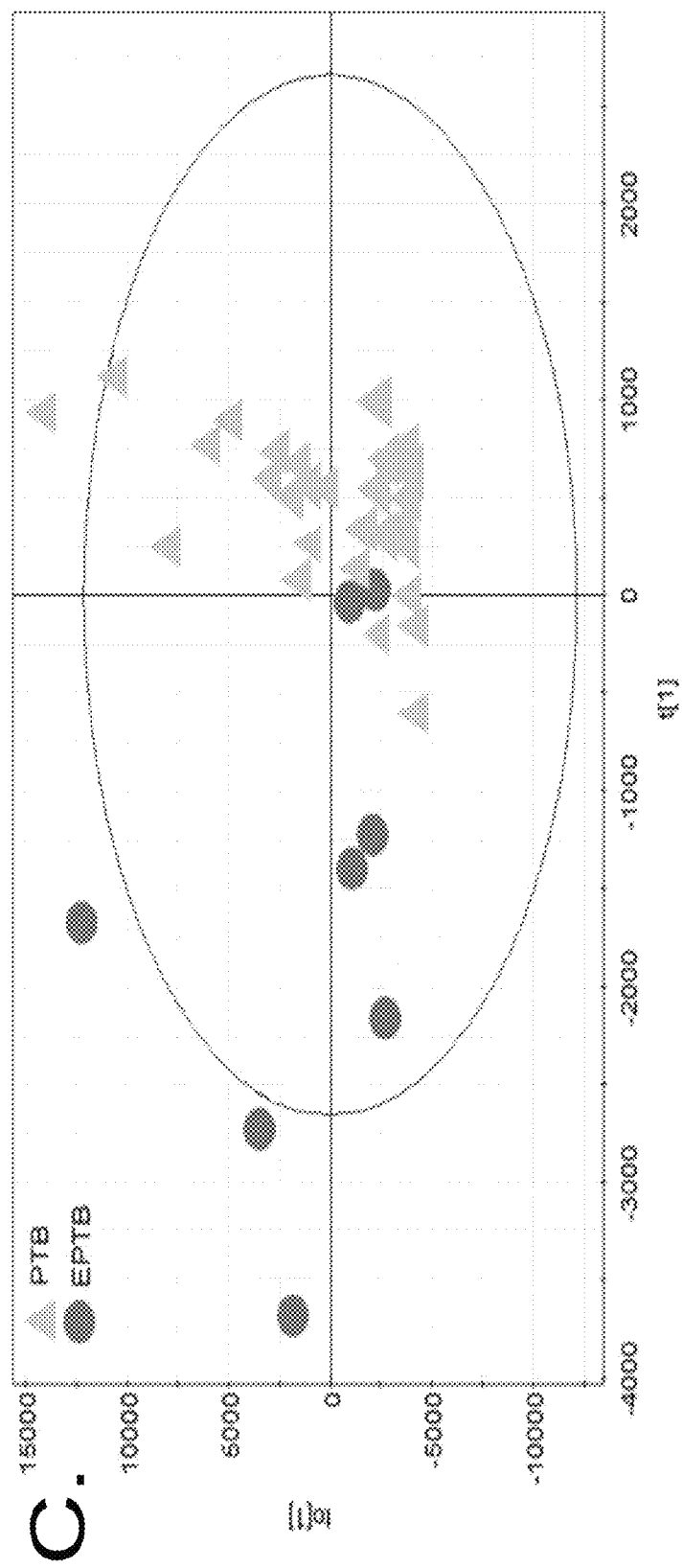

TB+ data was sorted by PCA to differentiate PTB or EPTB from TB− (including LTBI) (FIG. 11). This analysis eluded that several peptides contribute to PTB and EPTB peptide fingerprints. Additional statistical analyses supported this, and demonstrated 4 and 9 peptides that significantly distinguish PTB or EPTB from TB−, respectively (FIG. 8). When compared directly to each other, PTB and EPTB can be clearly separated by discriminant analysis (FIG. 11) signifying the importance of including markers that represent multiple forms of active disease. This observation corroborated those displayed by the binary heat map which depicts the unique peptide profile associated with multiple disease states.

Supplemental Methods

Figure 12:
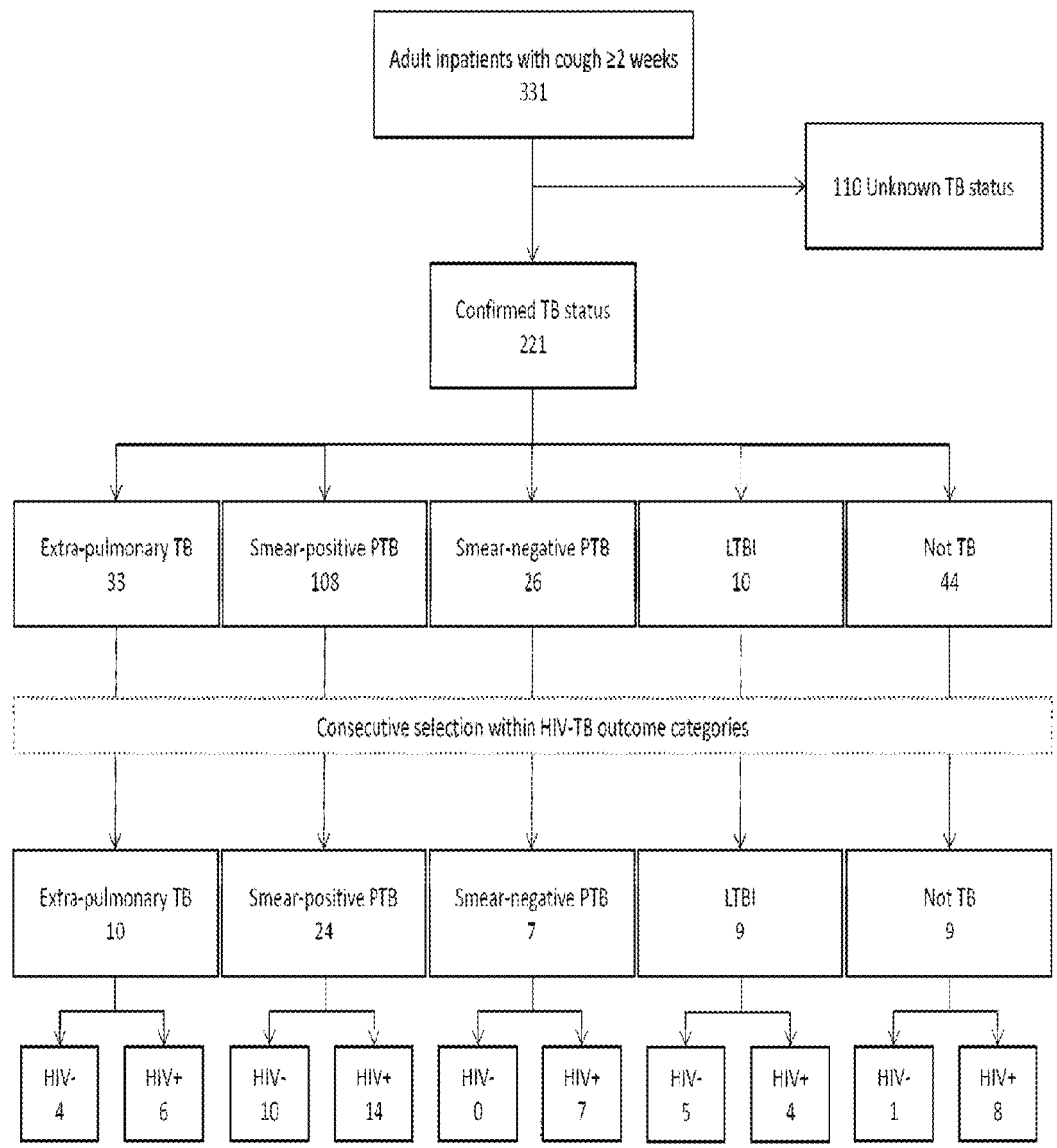
FIG. 12. Flow diagram describing patient enrollment in the TB evaluation sample at Mulago Hospital, Kampala, Uganda.

Patients were sampled from the overall cohort of patients with unexplained cough for ≥2 weeks, based on the following reference standard definitions for TB outcome classification (see FIG. 12).

Confirmed Active TB Diagnosis Categories

All patients diagnosed as TB-positive fit into one of the following categories:
 1. Culture-positive pulmonary TB (PTB)
    ≥1 positive sputum or bronchoalveolar lavage (BAL) culture with >50 colony-forming units (CFU) on solid Lowenstein-Jensen media
 2. Culture-positive AND smear-or TB nucleic-acid amplification test (NAAT)-positive pulmonary TB Culture with <50 CFU but accompanied by either ≥1 positive direct Ziehl-Nielsen (DZN) or LED fluorescence (FM) smear microscopy, or a positive GeneXpert MTBB/RIF results on sputum
3. Not culture-positive but smear-positive and TB NAAT-positive pulmonary TB
No positive cultures but ≥1 positive DZN or LED FM smear microscopy and a positive GeneXpert MTBB/RIF result on sputum
4. Extra-pulmonary TB
Fulfills none of the criteria for pulmonary TB, but has ≥1 of the following:
Fine-needle lymph-node aspirate with positive AFB-smear examination
Cerebrospinal, pericardial, peritoneal, or pleural fluid with exudative fluid chemistries and/or lymphocyte-predominant cell differential Confirmed Non-TB Diagnosis Categories
Fulfills none of the criteria for confirmed active TB above, and
1. Not Active TB
≥2 negative Mtb cultures; no positive Mtb cultures, AFB smears, or GeneXpert results; and showed radiographic and/or clinical improvement by 2 months of follow-up without receiving TB therapy
i. Latent TB Infection (LTBI) status:
1. LTBI-positive: Not TB, and a positive T-SPOT result by FDA criteria.
2. LTBI-negative: Not TB, and a negative T-SPOT result by FDA criteria.

Unknown TB status
Fulfills none of the criteria for confirmed active TB or confirmed not TB categories; <2 negative Mtb cultures.

Discussion. Identifying a biomarker panel for diagnosis of active tuberculosis is of paramount importance. Towards this goal, the applicants generated multiplex peptide bioassays for 76 peptides representing proteins initially discovered in exosomes by shotgun proteomics using tandem MS. The aim was to optimize MRM methods so that screening could be expanded to larger sample populations. The work described here provides the foundation for qualifying exosome-based Mtb-specific biomarkers for the detection of active TB using an MRM-MS platform. MRM-MS is a technique with high analytic sensitivity and specificity which takes advantage of a triple quadrupole MS system. Designing MRM assays requires a priori knowledge of proteins and peptides of interest, from which a combination of unique precursor/transition ion pairs allow us to confidently identify the target at low feMtbomolar/high attomolar levels in a complex matrix. In addition to its exquisite sensitivity, MRM-MS has several additional advantages over traditional proteomic screening and validation assays, namely, the ability to identify dozens of analytes in a single assay, as well as the ability to confirm or validate discovery efforts without the reliance on available immune reagents. Further, MRM assays can be applied to samples that were eliminated from shot-gun or discovery platforms due to interference of contaminating proteins. This aspect is exemplified by our human discovery efforts, in which by LC-MS/MS only 8 Mtb proteins were confidently identified and included in our multiplex MRM analyses. In our MRM assays proteins originating from the host are disregarded and only peptides of interest belonging to Mtb are selected for fragmentation and detection; this enabled us to mine for and generate specific peptide bioassays to validate biomarker candidates identified in multiple original discovery experiments. From this, 22 of the 33 proteins identified during the discovery phase were confidently identified in human sera.

A serodiagnostics test has been a long-standing goal of the TB community; however, analysis of multiple, commercial serodiagnostic assays has consistently shown them to have poor specificity and/or sensitivity. Therefore, the WHO has advised against the use of all currently available commercial TB serodiagnostic tests. As previously observed, and confirmed by our work, the antigenic repertoire of Mtb is dynamic, based on disease stage, and this likely translates to the heterogeneous antibody responses previously reported. Whether a final diagnostic assay targets bacterial peptides or host responses to bacterial products, an assay in which multiple biomarkers are monitored will have improved performance. Limitations of both serologies have been noted in severely immunocompromised patients, notably those infected with HIV. The data presented here indicate that detection of Mtb biomarkers in exosomes may not rely on the immunocompetence of the host as no difference was observed between patients co-infected with HIV ($p=0.7073$), suggesting a potential n added benefit to exosome-based applications over current diagnostics that measure host responses. Additional studies in a larger sample set are necessary to confirm this observation. Further, studies are required to determine if the exosome response in children is as robust. A non-sputum-based diagnostic could benefit this patient population, as sputum is often challenging to collect from children.

Here, the applicants report a proteomic workflow, which includes assay development, optimization, and determination of cut-off values for 76 of our lead candidate peptide biomarkers. Analysis of our results led to the reduction of candidate serum biomarkers from 76 to 30 peptides. These final candidates will be combined into an MRM assay that will enable relatively high throughput screening of exosomes from TB patients and expand our investigations on these promising biomarkers. In addition to furthering this goal, these assays may be used to address questions regarding pathogenesis of Mtb, possibly explaining the diverse disease spectrum observed in TB patients. Preliminary analysis of a small sample of patients suggests the ability to stratify disease stage by biomarker detection, particularly between EPTB and TB patients. Expansion of these studies may provide additional support for specific biomarkers to understand variations in disease manifestations, and may be further exploited to identify LTBI patients at risk of development of active disease. Further, this report deployed samples derived from a clinic in Uganda for our preliminary evaluation. While this an appropriate starting-point for assay development, samples from other geographical regions should be included in future studies to address the effects of antigenic variation between Mtb clades and its influence on the exo-proteome profile.

In this study, MRM-MS was applied to a simplified fraction of serum to detect only mycobacterial proteins enriched within exosomes. The applicants hypothesize that the majority of mycobacterial proteins, at least in serum, will be localized to exosomes. This is based on the fact that Mtb is an intracellular pathogen which is known to release mycobacterial components from the phagosome during infection. However, the mechanism by which mycobacterial components are trafficked from the multi-vesicular body onto exosomes is presently unknown. Nevertheless, the purification of exosomes from serum would be expected to greatly enrich for mycobacterial components including proteins and thus be a good source for biomarker identification. Since the exosomes reflect what mycobacterial proteins were being produced at the time serum was isolated it is not surprising that there would be variation in the type of proteins identified in the MRM between patient populations especially when comparing pulmonary TB to EPTB. Variation in host genetics, strains of mycobacteria, time post-infection, state of the immune response, etc. will all lead to changes in mycobacterial protein expression and therefore changes in mycobacterial proteins present in exosomes. Nevertheless, by using multiple proteins/peptides highlighted in this study we hope to develop a "biosignature" that is capable of identifying active TB patients and perhaps distinguish different patient populations including subclinical pulmonary TB and LTBI.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A protein signature diagnostic of an active *M. tuberculosis* infection wherein the protein signature of the active *M. tuberculosis* infection comprises proteins present on or in exosomes, the proteins comprising the combination of Rv0129c, Rv0440, Rv0934, Rv1837c, Rv1860, Rv1886c, Rv1980c, Rv2031c, Rv2376c, Rv3248, Rv3418c, Rv3441c, Rv3804c, and Rv3841, and acetonitrile or formic acid.

2. The protein signature of claim 1 wherein the protein signature is in contact with acetonitrile.

3. The protein signature of claim 1 wherein the protein signature is in contact with formic acid.

4. The protein signature of claim 1 comprising about 3% acetonitrile.

5. The protein signature of claim 1 comprising about 0.1% formic acid.

6. The protein signature of claim 3 comprising about 3% acetonitrile and 0.1% formic acid.

7. The protein signature of claim 1 further comprising Rv0350, Rv1469, Rv2244 and Rv2626c.

8. The protein signature of claim 1 further comprising Rv2626c.

9. A protein signature diagnostic of an active *M. tuberculosis* infection wherein the protein signature of the active *M. tuberculosis* infection comprises proteins present on or in exosomes, the proteins comprising the combination of Rv0129c, Rv0440, Rv0934, Rv1837c, Rv1860, Rv1886c, Rv1980c, Rv2031c, Rv2376c, Rv3248, Rv3418c, Rv3441c, Rv3804c, and Rv3841, and sodium dodecyl sulfate.

10. The protein signature of claim 8 further comprising Rv0350, Rv1469, Rv2244 and Rv2626c.

11. The protein signature of claim 8 further comprising Rv2626c.

* * * * *